(12) United States Patent
Lebolt et al.

(10) Patent No.: US 10,772,782 B2
(45) Date of Patent: Sep. 15, 2020

(54) DYNAMIC TENSIONING ORTHOSIS AND RELATED METHOD OF USE

(71) Applicant: Spectrum Health Innovations, LLC, Grand Rapids, MI (US)

(72) Inventors: James R. Lebolt, Ada, MI (US); Eric J. VanMiddendorp, Grand Rapids, MI (US); Timothy D. Stoepker, Grand Rapids, MI (US); Isaac Running, Missoula, MT (US); Robert Ball, West Olive, MI (US)

(73) Assignee: Spectrum Health Innovations, LLC, Grand Rapids, MI (US)

( * ) Notice: Subject to any disclaimer, the term of this patent is extended or adjusted under 35 U.S.C. 154(b) by 376 days.

(21) Appl. No.: 15/795,795

(22) Filed: Oct. 27, 2017

(65) Prior Publication Data

US 2018/0116893 A1 May 3, 2018

Related U.S. Application Data

(60) Provisional application No. 62/414,153, filed on Oct. 28, 2016.

(51) Int. Cl.
*A61F 5/01* (2006.01)
*A61H 1/02* (2006.01)
(Continued)

(52) U.S. Cl.
CPC ........... *A61H 1/006* (2013.01); *A61F 5/0104* (2013.01); *A61F 5/0118* (2013.01);
(Continued)

(58) Field of Classification Search
CPC .... A61F 5/0104; A61F 5/0109; A61F 5/0118; A61F 5/013; A61F 5/37; A61F 5/3723;
(Continued)

(56) References Cited

U.S. PATENT DOCUMENTS

| 3,906,944 A | 9/1975 | Christen |
| 4,644,939 A | 2/1987 | Coleman |

(Continued)

OTHER PUBLICATIONS

Donjoy Sully Shoulder Stabilizer—http://www.djoglobal.com/products/donjoy/sully-shoulder-stabilizer (downloaded Oct. 10, 2017).
(Continued)

*Primary Examiner* — Keri J Nelson
(74) *Attorney, Agent, or Firm* — Warner Norcross + Judd LLP

(57) ABSTRACT

An orthosis includes dynamic tensioning elements, recreating and/or improving on the load sharing typically provided by soft tissue, such as ligaments, tendons, muscle and a capsule at a joint of a patient or wearer, thereby providing support and preventing further injury from joint instability and/or joint laxity. The orthosis can support a glenohumeral joint of the shoulder brace and can prevent additional injury from various shoulder instabilities, for example, anterior, inferior, posterior and/or multidirectional instabilities. This can be accomplished by dynamically tensioning posterior, anterior and/or humeral head straps of the orthosis. The straps can be primarily adjustable only in tension forces stored there within, rather in orientation relative to the shoulder. This can simplify setup and use, and can ensure the orthosis has a low profile. Related methods of use also are provided.

18 Claims, 18 Drawing Sheets

(51) Int. Cl.
*A61H 1/00* (2006.01)
*A61F 5/37* (2006.01)

(52) U.S. Cl.
CPC .............. *A61H 1/0281* (2013.01); *A61F 5/37* (2013.01); *A61H 2201/1616* (2013.01)

(58) Field of Classification Search
CPC .... A61F 5/3738; A61F 5/3746; A61F 5/3753; A41D 13/0007; A41D 13/0015; A41D 13/0512; A61H 1/006; A61H 1/02; A61H 1/0274; A61H 1/0281
USPC ............................................ 602/20; 482/124
See application file for complete search history.

(56) References Cited

U.S. PATENT DOCUMENTS

| | | | |
|---|---|---|---|
| 4,735,198 A | 4/1988 | Sawa | |
| 4,862,878 A | 9/1989 | Davison | |
| 5,188,587 A | 2/1993 | McGuire | |
| 5,403,268 A | 4/1995 | Clement | |
| 5,520,620 A | 5/1996 | Johnson | |
| 5,606,745 A * | 3/1997 | Gray | A41D 13/0015 2/227 |
| 5,628,725 A | 5/1997 | Ostergard | |
| 5,857,990 A | 1/1999 | Maas | |
| 6,079,055 A | 6/2000 | Mencel | |
| 6,101,637 A | 8/2000 | Lessard | |
| 6,106,493 A | 8/2000 | Rozell | |
| 6,132,393 A | 10/2000 | Lundberg | |
| 6,152,891 A | 11/2000 | Carlson | |
| 6,202,214 B1 | 3/2001 | Light | |
| 6,306,111 B1 | 10/2001 | Dean | |
| 6,322,528 B1 | 11/2001 | Kania | |
| 6,398,746 B2 | 6/2002 | Bramlage et al. | |
| 6,691,327 B1 | 2/2004 | Meyer | |
| 6,733,467 B2 | 5/2004 | Kania | |
| 6,941,586 B1 | 9/2005 | Weinhold | |
| 7,081,101 B1 | 7/2006 | Sawa | |
| 7,135,005 B2 | 11/2006 | Kania | |
| 7,207,963 B2 | 4/2007 | Kania | |
| 7,255,679 B2 | 8/2007 | Kania | |
| 7,320,669 B2 | 1/2008 | Campbell | |
| 7,615,019 B2 | 11/2009 | Nordt | |
| 7,615,020 B2 | 11/2009 | Nordt | |
| 7,615,021 B2 | 11/2009 | Nordt | |
| 7,615,022 B2 | 11/2009 | Nordt | |
| 7,615,023 B2 | 11/2009 | Nordt | |
| 7,615,027 B2 | 11/2009 | Nordt | |
| 7,618,389 B2 | 11/2009 | Nordt | |
| 7,621,881 B2 | 11/2009 | Nordt | |
| 7,637,884 B2 | 12/2009 | Nordt | |
| 7,708,708 B2 | 5/2010 | Nordt | |
| 7,785,281 B2 | 8/2010 | Scott | |
| 7,790,814 B2 | 9/2010 | Basheer et al. | |
| 8,192,382 B2 | 6/2012 | Huang | |
| 8,287,478 B2 | 10/2012 | Ostergard et al. | |
| 8,672,864 B2 | 3/2014 | Nordt | |
| 9,895,569 B2 * | 2/2018 | Yao | A63B 69/0028 |
| 2004/0193082 A1 | 9/2004 | Cofre | |
| 2004/0193086 A1 | 9/2004 | Cofre | |
| 2005/0261113 A1 * | 11/2005 | Wilkinson | A63B 21/00069 482/124 |

OTHER PUBLICATIONS

Kinesio—Kinesio Tape—https://kinesiotaping.com/about/ (downloaded Oct. 10, 2017).
Shock Doctor—Shock Doctor Ultra Support with Stability Control System—https://www.shockdoctor.com/ultra-shoulder-support-with-stability-control (downloaded Oct. 10, 2017).
EVS—EVS SB03 Shoulder Brace—http://evs-sports.com/catalog/product/view/id/960/s/sb03-shoulder-brace/category/86/ (downloaded Oct. 10, 2017).
McDavid—McDavid Light Shoulder Support—http://www.mcdavidusa.com/shoulder-wrap (downloaded Oct. 10, 2017).
Cadlow—Cadlow Shoulder Stabilizer—http://www.dmsystems.com/cadlow.html (downloaded Oct. 10, 2017).
Donjoy—DJO Shoulder Stabilizer—http://www.djoglobal.com/products/donjoy/donjoy-shoulder-stabilizer (downloaded Oct. 10, 2017).
Donjoy—Reaction Knee Brace—http://www.djoglobal.com/products/donjoy/reaction-web-knee-brace (downloaded Oct. 10, 2017).
Donjoy—DJO Wrist Brace with BOA—http://www.djoglobal.com/products/exos/wrist-brace-boa (downloaded Oct. 10, 2017).

* cited by examiner

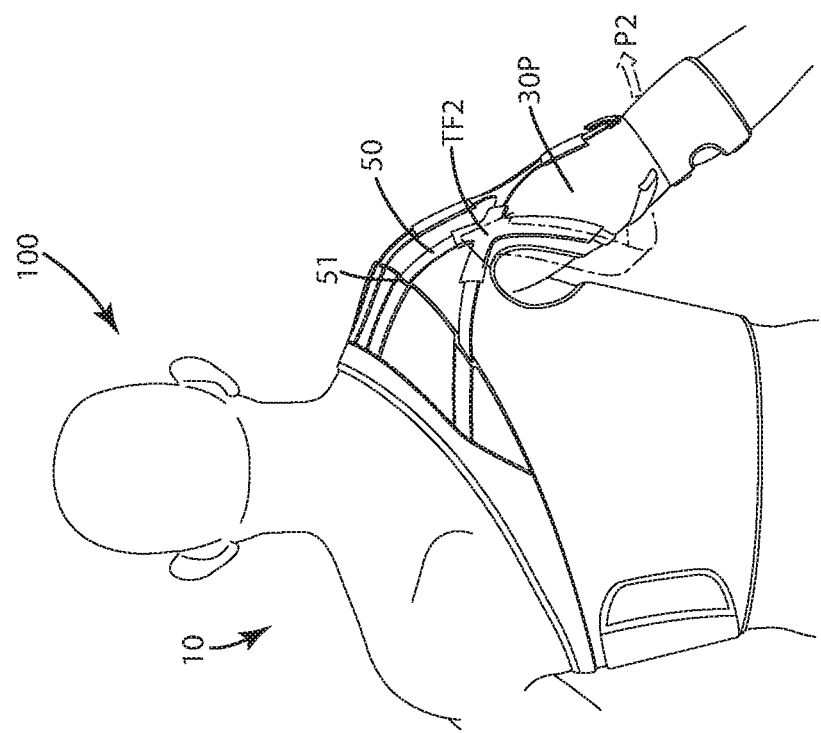
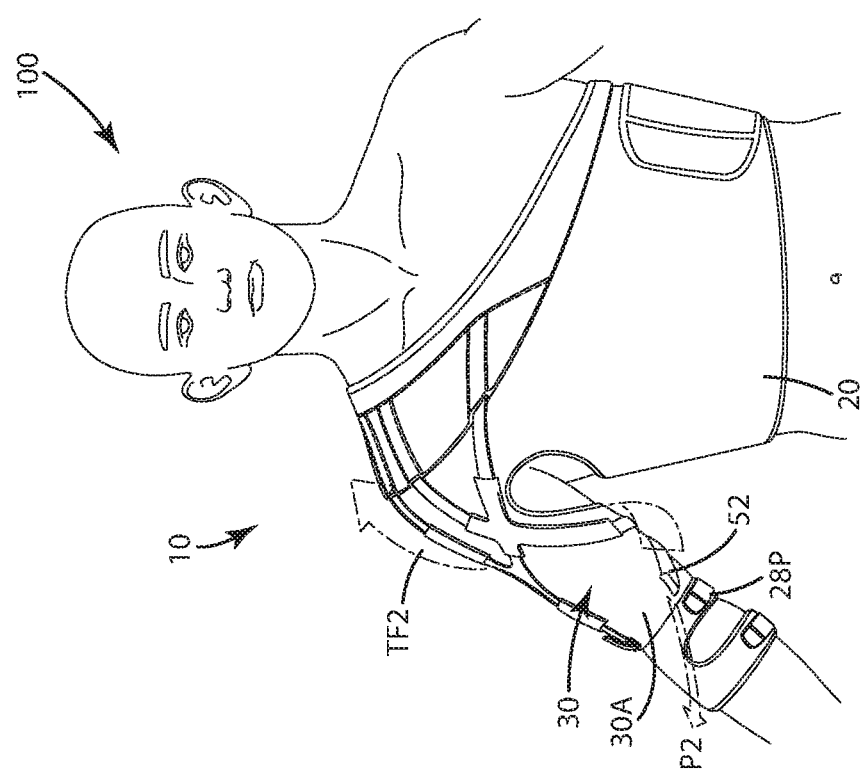
Fig. 8
Fig. 9

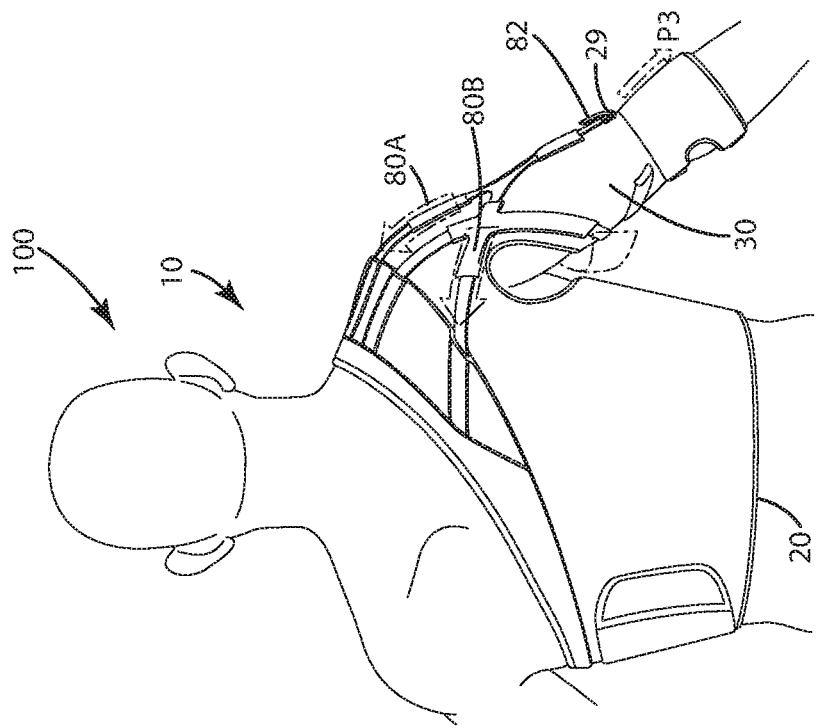
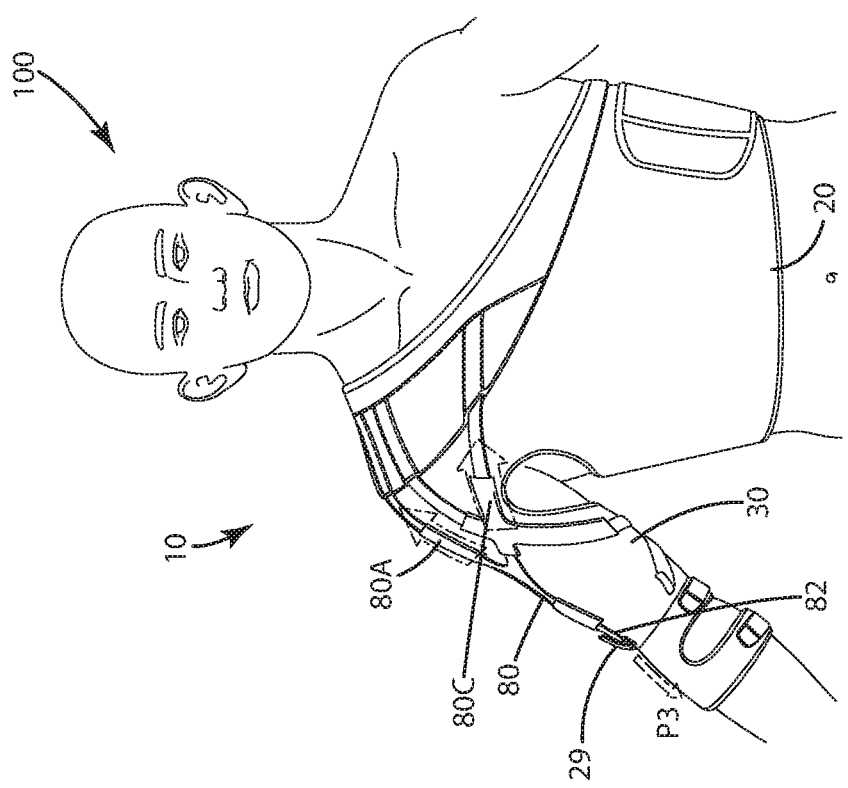

DYNAMIC TENSIONING ORTHOSIS AND RELATED METHOD OF USE

BACKGROUND OF THE INVENTION

The present invention relates to a dynamically tensioned orthosis configured to stabilize a human joint, for example, a human shoulder, elbow, wrist, hip, knee or ankle.

Over time, the joints of a human body invariably are subject to conditions that can lead to joint deterioration, immobility and pain. In some cases, a joint may undergo trauma; in other cases, with age and extensive use, a joint may sustain inherent joint laxity. In both of these cases, the joint can experience a disruption in static and dynamic support.

Human joints can be supported statically, dynamically and via negative pressure. To provide static support, a joint can include soft tissues such as muscles, ligaments, tendons and a capsule. A disruption of any of these static supports, either due to trauma or joint laxity may result in a decrease in the load sharing of those elements. As an example, where a joint ligament is compromised, it likely will be unable to effectively resist joint translation, which in turn can decrease joint stability.

A particular human joint that is prone to disruption due to its complex nature is the shoulder, which comprises the glenohumeral joint. Every year 4.5 million people seek help for shoulder pain, with 2 million seeking help for rotator cuff injuries. Nearly 250,000 people have rotator cuff surgery each year. Over 7.5 Million people go to their doctor for a shoulder problem annually, including shoulder and upper arm sprains and strains. Shoulder injury to the rotator cuff, labrum, or other muscles or tendons supporting the glenohumeral joint can lead to shoulder laxity (instability). If a patient has a weakened or unstable shoulder capsule that is not properly supported, it can lead to additional breakdown and injury.

With joint laxity, one will typically require rehabilitation, or, depending on the severity of the injury, surgery to fix the problem. Anterior/inferior instability is the most common problem (about 60%), and posterior instability (about 20%) is less common but does occur most frequently in football lineman. Multi-directional instability makes up the remaining 20% or so of cases.

The glenohumeral joint of the shoulder is invariably unstable due to the convex articulation of the humeral head with the concavity of the glenoid fossa. The humeral head is covered by less than a third of the glenoid fossa throughout the joint's entire range of motion. While the glenohumeral ligaments, labrum and capsule as well as the articular surface provide static support. These tissues can be disrupted due to traumatic injury or over time with inherent joint laxity. Accordingly, such compromised ligaments are unable to effectively resist joint translation, which decreases joint stability. Specifically, the inferior glenohumeral (GHL) (with its anterior and posterior bands), the superior GHL, and the coracohumeral GHL are all important components of the complex. When these respective ligaments are compromised, this can lead to anterior, posterior, inferior and/or multidirectional shoulder instabilities.

The most common cause of shoulder pain in athletes, and in particular young athletes, is shoulder instability and not, as frequently misdiagnosed some underlying rotator cuff injury, impingements or bursitis. Rotator cuff injuries for youth athletes are extremely rare, whereas instability is common. (Savatsky, Gary, MD. "Shoulder Instability." Anterior Shoulder Instability (n.d.): n. pag. www.ossmc.com. 1 May 2006. Web. 9 Sep. 2015.)

To address shoulder instability, due to trauma, failed surgery or inherent joint laxity, or to protect or rehabilitate a successfully, surgically repaired shoulder, many healthcare providers resort to supporting the shoulder joint with an external orthopedic stabilization device. Such a device can provide external static, as well as dynamic, support to enable the individual to return to a previous level of function and hopefully reduce the risk of repeated injury. While there are a number of such devices in the market, many are complicated to use, have easily disrupted, misplaced or removed straps, and require a healthcare provider knowledgeable in the force vectors associated with particular instabilities to consistently install the device, particularly where the straps float over the shoulder. Further, most conventional shoulder braces do not address all forms of instability, for example, each of anterior/inferior instability, posterior instability, and straight compression laterally as well.

SUMMARY OF THE INVENTION

An orthosis and related method of use to provide support and prevent additional injury from joint instability is provided.

In one embodiment, the orthosis or device includes static and dynamic tensioning elements, recreating and/or improving on the load sharing typically provided by soft tissue, such as ligaments, tendons, muscle and a capsule at a joint of a patient or wearer, thereby providing support and/or preventing additional injury from joint instability.

In another embodiment, the orthosis can be in the form of a shoulder brace that is able to provide support and prevent additional injury from various shoulder instabilities, for example, anterior, inferior, posterior and/or multidirectional instabilities. This can be accomplished by applying anterior, posterior and lateral dynamic tensioning on the wearer's shoulder via the brace.

In still another embodiment, the shoulder orthosis can include a base, a sleeve and three individually and separately tensioned, built-in resistance straps. The straps can include an anterior strap, a posterior strap and an optional humeral head strap therebetween. Optionally, all of the straps can extend through anchors defining channels that enable the straps to slide within the channels, and that allow the direction of tension within the straps to be controlled, but that prevent the straps from sliding across the base to different orientations or along different routes which alters the tension force vectors exerted by the orthosis on the glenohumeral joint.

In even another embodiment, the anterior strap and posterior strap originate on the respective anterior or posterior of the base and/or wearer's shoulder, extend downward inferiorly, and wind under the arm to provide support. The anterior strap can originate on the front of the shoulder or anterior of the base, wind approximately 180 degrees around and under the wearer's arm, and terminate laterally or posterior to the wearer's elbow. This anterior strap can provide posterior support and also anterior/inferior support.

In yet another embodiment, the anterior strap can be adjustable in the tension stored within the strap, but non-adjustable in length or its orientation relative to the underlying base and sleeve, between a first anchor on an anterior of the base and a second anchor located inferior to the elbow.

In a further embodiment, the posterior strap can originate on the rear of the shoulder or posterior of the base, wind approximately 180 degrees under the wearer's arm, and terminate medially or anterior to the wearer's elbow. This strap can provide anterior/inferior support. Optionally, the tension force in this posterior strap can increase during external rotation to provide a "wind-up" effect, which also can increase proprioception, during external rotation and abduction, typically a vulnerable position for a wearer with anterior/inferior instability. In turn, the wearer can better perceive the vulnerability in that position due to the tension in the strap.

In still a further embodiment, the humeral head strap can provide uniform tension and can pull the humeral head directly into the glenohumeral joint. Optionally, the humeral head strap can include three strap sections that provide resistance across the anterior and posterior of the shoulder, as well as across the top of the shoulder to produce an evenly distributed tension or force across the shoulder. The sections can merge at a single location to form one strap, and can continue down the arm to a single adjustment anchor adjacent the wearer's elbow.

In still yet a further embodiment, the orthosis can include an anti-ride up element. In particular, the sleeve can include a lower portion configured to extend over a wearer's appendage inferior to the stabilized joint of the wearer. The anti-ride up element can be tapered along a length extending away from the upper portion so that the anti-ride up element prevents the sleeve from riding up the appendage of the wearer from an inferior position to a superior position along the appendage, thereby preventing that ride-up from cancelling the corrective tension force in the respective anterior, posterior and/or humeral head straps. Put another way, the anti-ride up element can take advantage of the natural narrowing of the forearm to prevent the sleeve from sliding up the arm due to the tension from the straps.

In even a further embodiment, the orthosis can include an anti-slide down element. In particular, the sleeve can include a bolster element that extends across the shoulder to prevent the orthosis from sliding down the arm. The bolster element can be in the form of a low-elasticity material, a reinforced additional layer and/or increased thickness of the base in that region. In some cases the bolster element can be constructed from a flexible material that is more rigid than the remainder of the base. The bolster element also can prevent bunching of the base and the sleeve due to preselected tension in the respective stability straps.

In still yet another embodiment, the shoulder orthosis can include a base, a sleeve, two individually and separately tensioned, built-in resistance straps, and a shoulder compression mitt. The straps can include an anterior strap and a posterior strap. The straps can extend through anchors in the form of channels defined by the sleeve that enable the straps to slide within the channels, and that allow the direction of tension within the straps to be controlled, but that prevent the straps from sliding across the base, other than along the route of the straps, or relative to the glenohumeral joint to different orientations or along different routes which alters the tension force vectors exerted by the orthosis on the glenohumeral joint.

In even another embodiment, the anterior strap and posterior strap originate on the respective anterior or posterior of the base and/or wearer's shoulder, extend laterally and/or downward inferiorly, and wind under or around the arm to provide support. Optionally, the anterior strap can originate on the front of the shoulder or anterior of the base or sleeve, extend laterally over the glenohumeral joint, crossing the joint at a first elevation toward the posterior of the base, reroute to extend anteriorly forward, back across the glenohumeral joint but inferior to the first elevation at a second lower elevation, then wind at least about 180 degrees around and under the wearer's arm, and terminate laterally, anteriorly or posteriorly to the wearer's elbow. This anterior strap can provide posterior support and also anterior/inferior support.

In yet another embodiment, the anterior strap can be adjustable in the tension stored within the strap, but non-adjustable in length or its orientation relative to the underlying base and sleeve, between a first anchor on an anterior of the base and a second anchor located inferior to the elbow. Optionally, the first anchor can include a superior/inferior connector constructed to attach the first anchor to the base at multiple locations at different elevations relative to the base.

In a further embodiment, the posterior strap can originate on the posterior of the shoulder or posterior of the base, extend laterally and/or downward inferiorly over the glenohumeral joint, crossing the joint at a first elevation toward the anterior of the base or sleeve, reroute to extend posteriorly rearward, back across the glenohumeral joint but inferior to the first elevation at a second lower elevation, then wind at least about 180 degrees around and under the wearer's arm, optionally crossing the anterior strap, and terminate laterally, anteriorly or posteriorly to the wearer's elbow. This strap can provide anterior/inferior support. Optionally, the tension force in this posterior strap can increase during external rotation to provide a "wind-up" effect, which also can increase proprioception, during external rotation and abduction, typically a vulnerable position for a wearer with anterior/inferior instability. In turn, the wearer can better perceive the vulnerability in that position due to the tension in the strap.

In still a further embodiment, the shoulder compression mitt can provide tension and can pull the humeral head directly toward and/or into the glenohumeral joint. The mitt can include a connector strap that extends from a location on the anterior of the base, across the shoulder laterally, to a location on the posterior of the base. Optionally, the mitt can include superior and inferior straps that connect the mitt to the base and/or the sleeve. Further optionally, the mitt can be integral with the straps. The straps and mitt can be configured to prevent bunching when the wearer's arm is raised, yet can and can provide resistance across the anterior and posterior of the shoulder, as well as across the top of the shoulder to produce an evenly distributed tension or force across the shoulder. In some cases, the mitt can be modular and removable or replaceable relative to the straps, sleeve and/or base.

The current embodiments provide an orthosis and related method of use that can comprehensively support a wearer's joint during movement, regardless of the type of instability in the wearer's joint. In some cases, the brace and its straps can be preconfigured on fixed, static routes across the brace so that the tension, rather than the location or orientation, of the straps can be altered or modified to address a particular instability in the joint. This can greatly simplify the donning and installation of the orthosis on the wearer. The orthosis also can functionally stabilize and assist the wearer based on their specific instabilities or conditions. The orthosis can have multiple use cases, including wearing the orthosis prophylactically to prevent injury, wearing the orthosis post-injury to continue working at an occupation or to extend an athlete's season, and also wearing the orthosis post-surgery for increased support and rehabilitation.

When in the form of a shoulder brace, the orthosis can be helpful in that it is fully functional, allowing a full range of motion while providing support for any form of shoulder instability, including anterior, inferior, posterior and/or multidirectional instabilities. Thus, the orthosis can be helpful in addressing one or more instabilities or laxity of the shoulder joint. The orthosis also can support a user who has damaged the supporting structures of the shoulder capsule, or experienced one or repeated glenohumeral subluxations or dislocations. Optionally, the orthosis restrains the humeral head from anterior, posterior and inferior translation, and/or applies compression to the glenohumeral joint. The orthosis also can stimulate proprioceptive awareness of movement of the glenohumeral joint.

When used in sports, the orthosis can be worn by football, rugby, lacrosse and hockey players. Of course, virtually any other athlete can wear the orthosis as well. For example, basketball or soccer players with repeated subluxation, instability, or dislocations may wear this brace but less frequently. In addition, manual laborers and other workers can utilize the orthosis to assist in movement and comfort of an affected joint.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1A is a section view taken along lines 1A-1A of FIG. 1;

FIG. 2A is a section view taken along lines 2A-2A of FIG. 2;

FIG. 8 is a front view of the shoulder brace with a posterior strap in a tensioning mode to address anterior and inferior instability of the glenohumeral joint;

FIG. 9 is a rear view of the shoulder brace with an posterior strap in a tensioning mode to address anterior and inferior instability of the glenohumeral joint;

FIG. 10 is a front view of the shoulder brace with the anterior strap and the humeral straps in a tensioning mode to address instability of the glenohumeral joint;

FIG. 11 is a rear view of the shoulder brace with the posterior strap and the humeral straps in a tensioning mode to address instability of the glenohumeral joint;

DESCRIPTION OF THE CURRENT EMBODIMENTS

Figure 12:
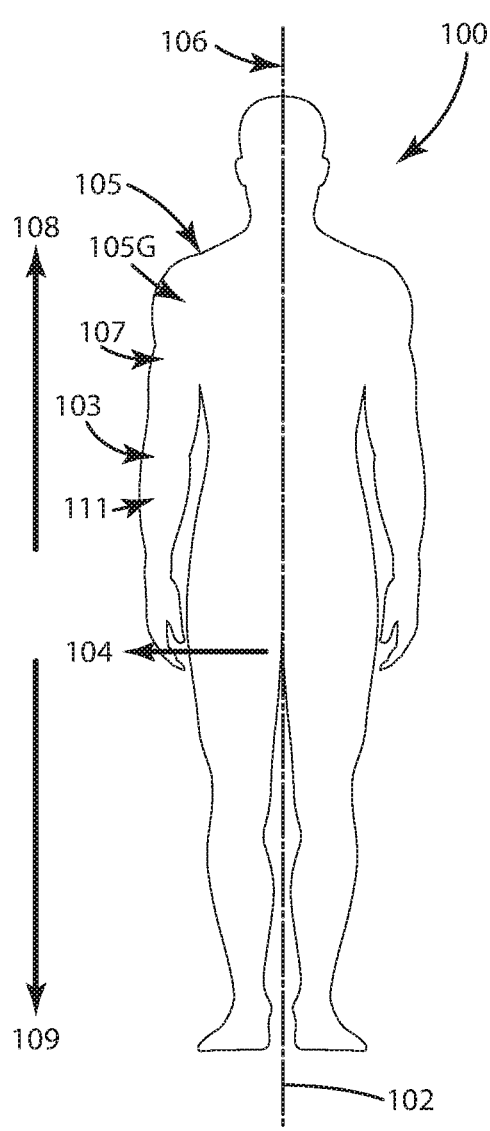
FIG. 12 is a front view of a wearer illustrating directions relative to features in association with the wearer's anatomy.
Figure 13:
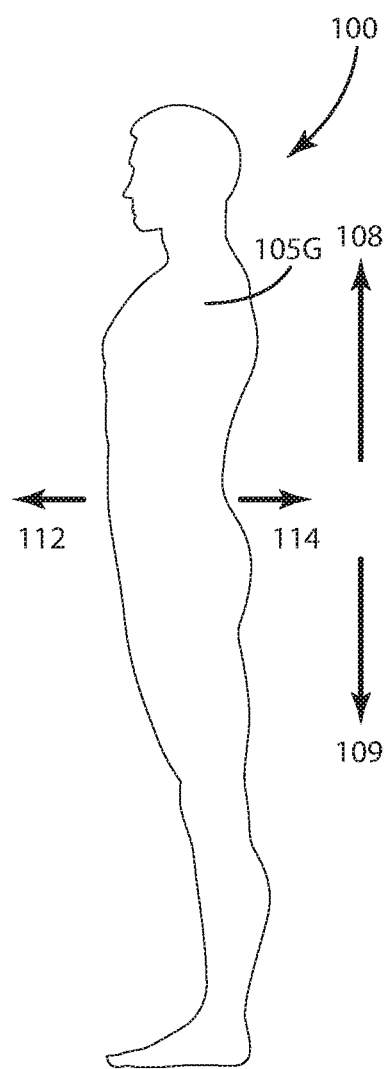
FIG. 13 is a side view of the wearer illustrating directions relative to features in association with the wearer's anatomy.

A current embodiment of the orthosis is illustrated in FIGS. 1-11, and generally designated 10. The orthosis shown in the current embodiment is in the form of a shoulder brace, configured to dynamically stabilize and support the glenohumeral joint 105G in a shoulder 105 of a wearer 100 (FIGS. 12-13). Although the orthosis 10 is shown in this application, it is well-suited for addressing support and instability issues in a variety of different joints, for example, the elbow, wrist, hip, knee and ankle joints with appropriate modifications to the orthosis to address the same.

Generally, the orthosis 10 includes a base 20 including a sleeve 30. The base 20 can secure the orthosis to the torso 113, while the sleeve can secure the orthosis to the arm and over the shoulder 105. An anterior strap 40 and a posterior strap 50 are secured to the base, and wrap around the arm as further described below. The anterior strap 40 is guided along a first fixed route or pathway FR1 by an anterior first anchor 60, while the posterior strap is guided along a second fixed route or pathway FR2 by a posterior first anchor 70. Optionally, the anterior strap and posterior strap are fixed and permanently constrained along these fixed routes FR1 and FR2 so that the wearer cannot deviate or modify those routes relative to the underlying sleeve and/or base. Of course, in some applications, the respective anchors 60 and 70 can be movable and/or replaceable along the exterior of the sleeve to facilitate such modification.

The anterior 40 and posterior 50 straps can be constructed from an elastic material and can be primarily adjustable only in tension force stored in those straps, that is, they optionally cannot be reoriented or moved around relative to other portions of the sleeve and/or base. With this construction, a wearer or user can simply adjust the tension forces TF1 or TF2 in the respective anterior 40 and posterior 50 straps to provide a desired dynamic tensioning of those straps and attendant support to the glenohumeral joint 105G. A user need not be concerned with where the ends of the straps are located or anchored to the base and/or sleeve because the respective anchors, as discussed below, are relatively fixed in their spatial orientation relative to one another, as are the ends of the straps.

Optionally, as described further below, the orthosis 10 also can include a humeral head strap 80. This strap can be configured to provide uniform tension and pull the humeral head of the wearer directly into the glenohumeral joint 105G of the shoulder 105. The humeral head strap can include multiple straps or sections.

Referring to FIGS. 12-13, any reference to body position or direction herein can be made with respect to the body 100 of a wearer in the anatomical positions there. References to the position of the orthosis 10 with respect to body 100 of the wearer, as well as references to movement can be made using standard anatomical position and movement terms. For example, the term superior 108 is a direction closer to a head of the wearer, the term inferior 109 is a direction farther from the head of the wearer, the term medial describes a direction 106 closer to the midline or sagittal plane 102 of the body 100, while the term lateral describes a direction 104 is farther from the midline or sagittal plane 102. The term anterior 112 describes a direction toward the front of the body 100 and the term posterior 114 describes a direction toward the back of the body 100. When describing bodily movements, abduction describes motion away from midline 102, and the term adduction describes motion toward midline 102. Flexion refers to motion that reduces a joint angle, and extension refers to motion that increases a joint angle.

The shoulder 105 includes the glenohumeral joint 105G which is relatively complex and capable of rotation in multiple planes when the arm is moved relative to the torso 113. As exemplary types of rotation, "external rotation" or "internal rotation" of the shoulder 105 occurs when the forearm or lower arm 111 is respectively displaced away from or toward the torso 113 while the position of the upper arm 107 is maintained fixed against the side of the torso 113 and the elbow 103 is flexed at 90°. "Abduction" or "adduction" of the glenohumeral joint 105G occurs when the upper arm 107 extends outward to the side and displaces away from or toward the torso 113. "Flexion" or "extension" of the joint 105G occurs when the entire arm 107, 103, 111 is extended forward and is displaced respectively toward or away from the torso 113.

The components of the orthosis 10, including the base 20, the sleeve 30, stability straps 40 and 50, as well as the various anchors will now be described in further detail. The base 20 includes a base anterior 22 which can be disposed across the anterior of the wearer's torso 113. The base anterior 22 is joined with the base posterior 24 which can be disposed across the posterior of the wearer's torso 113. These components can be integral with one another or can be stitched portions of textile or performance material. Some suitable materials from which the base and sleeve can be constructed can include Neoprene, BIOSKIN™ available from Bio Skin of Ashland, Oreg., knitted or woven fabrics, engineered mesh, engineered textiles, and similar materials that are generally breathable and durable. As shown, the base can include a closure 23 to join the base anterior and the base posterior, in applications where the base anterior and base posterior are not integral with one another. This base closure can include a pair of fasteners, one associated with the base anterior, the other associated with the base posterior, that can close and secure the respective ends of those components to one another. The fasteners can be hook-and-loop fasteners, buttons, clips, clasps, buckles and the like. Optionally, the fasteners can be deleted and the base can be in the form of a t-shirt or shirt having panels permanently stitched together.

Figure 1:
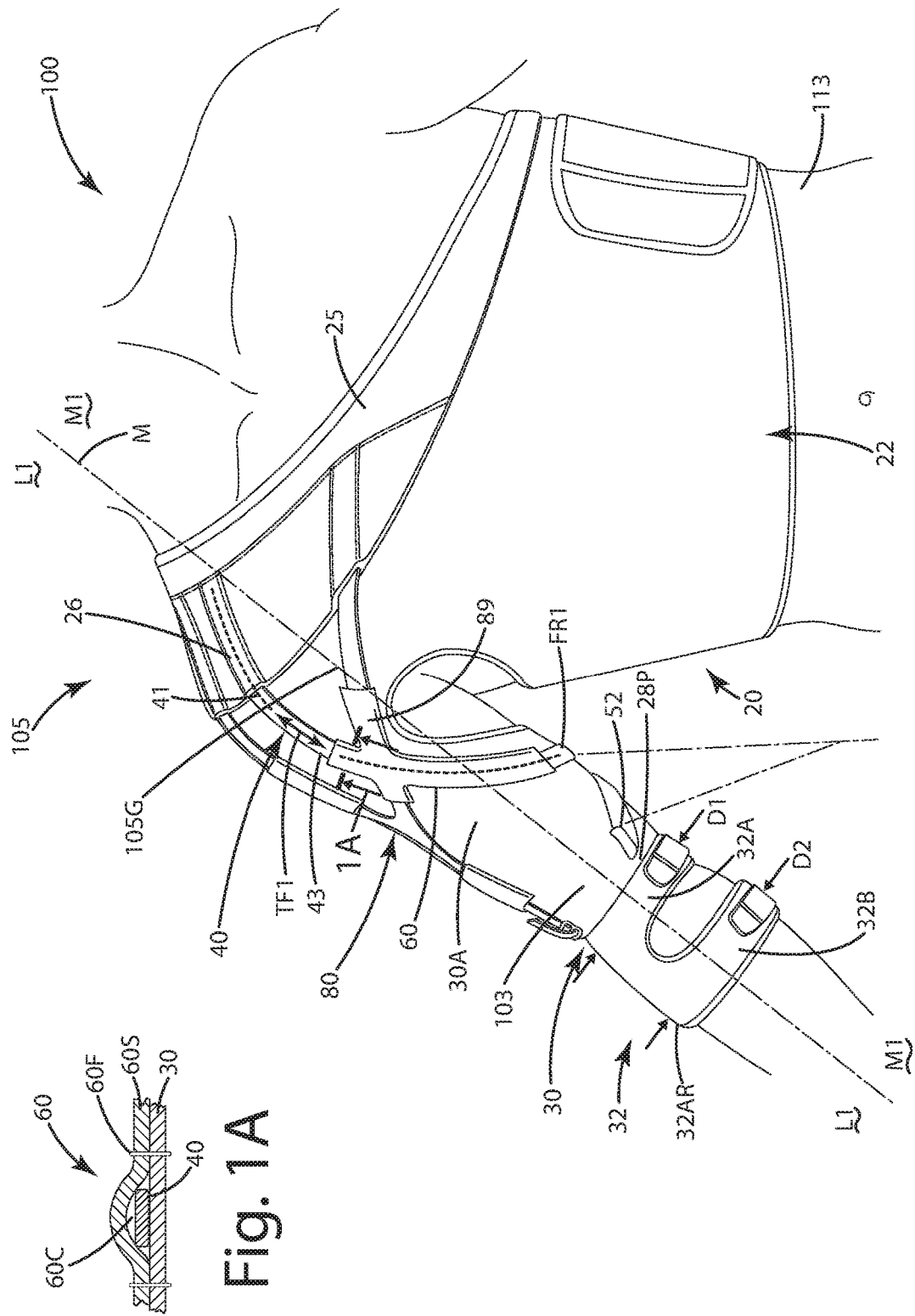
FIG. 1 is a front perspective view of the orthosis in the form of a shoulder brace of a current embodiment.
Figure 2:
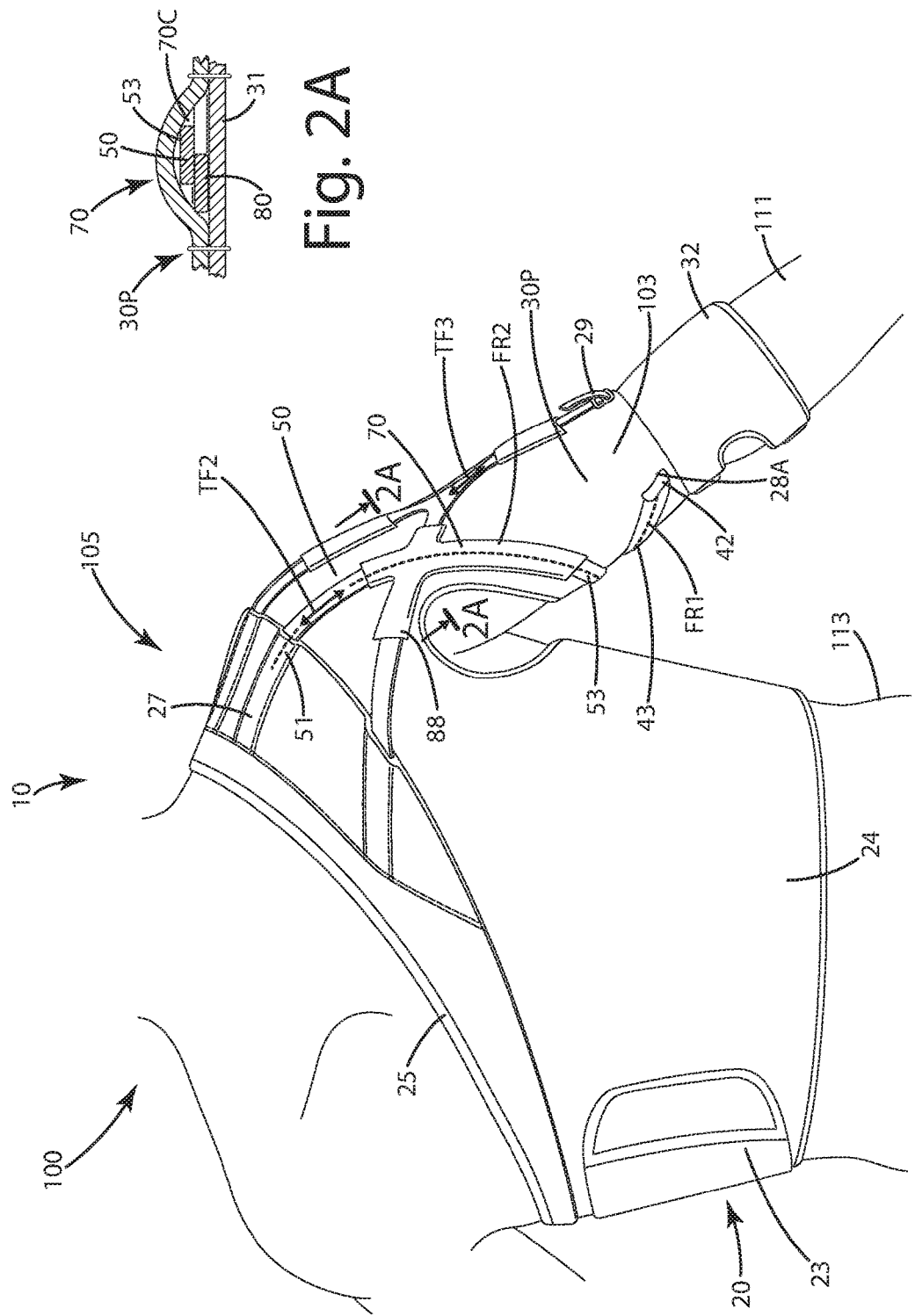
FIG. 2 is rear perspective view of the shoulder brace.

As shown in FIGS. 1 and 2, the base 20 can include a bolster element 25. The bolster element 25 can extend adjacent and/or over the base anterior 22, superiorly upward and over the shoulder 105, and then inferiorly downward adjacent the base posterior 24. This bolster element 25 can be disposed superior to the anterior deltoids, the lateral deltoids, and the posterior deltoids of the wearer. The bolster element can be stitched, sewn, fastened, or integrally formed with the base anterior and/or base posterior. The bolster element can be constructed from a different material than the remainder of the base anterior, the base posterior and the sleeve. For example, the bolster element can be constructed from a flexible material that is more rigid than the base anterior, the base posterior and/or the sleeve. In a further example, the bolster element can be constructed from neoprene, while the remainder of the base can be constructed from a textile fabric or a thinner, more flexible material. The bolster element can provide a structural reinforcement or support for the anterior, posterior and humeral head straps so that when those straps are under tension, they do not unintentionally pull on the portion of the base above the shoulder and move it significantly toward the elbow when under tension forces TF1, TF2 and/or TF3. In some cases, the bolster element 25 can be in the form of a silicone insert or plastic panel that is sewn into or otherwise disposed in or adjacent the base 20, optionally superior to and/or closer to the sagittal plane 106 than the above noted stability straps.

The anterior stability strap 40 can be secured at its first, anterior, or upper end 41 to the base 20, in particular to the bolster element 25. This can be done directly via a first anterior anchor 26. This first anterior anchor can be in the form of stitching, glue, cement, a hot weld, fasteners or other devices to fixedly and permanently secure the primary anterior and upper end 41 to the anterior base 20, optionally superior to the glenohumeral joint 105G and superior to the portions of the wearer's arm. This primary anterior end can be permanently secured to the base and/or bolster. By permanently secured or permanently joined, it means herein that the end or component cannot be removed from the base, bolster element or other component without destroying, damaging or impairing one or both of those components. The phrases "permanently secured" or "permanently joined" also can be used in conjunction with the joining of other elements of the orthosis as described below.

Optionally, although the first anterior anchor 26 is shown as being fixedly and permanently joined to the bolster, it can be temporarily or replaceably secured to the bolster and/or the base with fasteners such as hook-and-loop type fasteners, buttons or clips. Other anchors as described herein likewise can be temporarily or replaceably secured to respective components.

The posterior stability strap 50 can be secured at its secondary posterior end 51, also referred to as an upper or first end of the posterior stability strap, to the base 20, and in particular, to the bolster element 50. This can be done directly via a first posterior anchor element 27. Like the anterior anchor element, the posterior anchor element can be in the form of stitching, glue, cement, a hot weld, fasteners, rivets or other devices to fixedly and pivotally secure the secondary posterior end to the base and/or the bolster.

Optionally, although the first anterior anchor and the second posterior anchors are shown as stitching that permanently fixes the straps to the bolster, base anterior and base posterior, these anchors can include clips, adjusters, cam buckles, buckles, and/or hook-and-loop type fasteners. Further optionally, where the orthosis 10 includes the humeral head strap 80, the orthosis can include a humeral anterior anchor element 81C, a humeral posterior anchor element 81B and a humeral middle anchor element 81A. These humeral anchor elements can be secured to the base anterior, base posterior and therebetween respectively using the constructions mentioned above in connection with the anterior and posterior anchors of the other straps.

As shown in FIGS. 1 and 2, the base 20 includes a sleeve 30. The sleeve 30 originates at the shoulder 105 and extends downward, inferiorly along of the arm away from the shoulder. Though not shown, the base optionally can be joined with left and right sleeves to cover portions of both arms of the wearer. This can provide relatively constant compression over shoulders and torso of wearer to improve circulation and to enhance heat retention.

The sleeve 30 includes a sleeve upper arm portion 31 and a sleeve lower arm portion 32. The sleeve upper arm portion 31 can be in the form of a tube, which can circumferentiate the upper arm 107 of the wearer. Optionally, the sleeve upper arm portion 31 can be partially open in the axilla of the wearer's arm to enhance flexibility, venting and breathability. Sleeve upper arm portion 31 can further extend over the biceps and triceps of the wearer, on the respective anterior and posterior sides of the upper arm 107. In some cases, the sleeve upper arm portion 31 can also extend superior to the upper arm, over a portion of the shoulder 105 of the wearer 100.

The sleeve 30 can include a sleeve lower arm portion 32. The sleeve lower arm portion 32 can be in the form of a tube, which can circumferentiate the lower arm 111 of the wearer. The lower arm portion can extend to the lower arm and/or forearm where, past the elbow 103 of a wearer. The sleeve 30, optionally the sleeve lower arm portion 32, can include an anti-ride up element 32AR. The anti-ride up element can be tapered along a length extending away from the sleeve upper arm portion 31 so that a first dimension D1 of the anti-ride up element adjacent the upper arm portion is greater than a second dimension D2 of the anti-ride up element adjacent an opening at the lower end of the sleeve lower arm portion. With this taper and difference in dimension, the anti-ride up element 32AR can prevent the sleeve 30 from riding up an arm of the wearer from an inferior position to a superior position along the arm. This can be helpful in cases where the anterior 40, posterior 50 and humeral head 80 straps exert excessive tension forces therein, which tend to pull under force the lower arm portion 32 toward the upper arm portion 31 and/or shoulder, in a superior direction.

While the anti-ride up element 32AR can be in the form of a tube having varying dimensions, it also can be the form of the lower arm portion 32 having adjustable straps 32A and 32B as shown in FIG. 1. The straps to be tightened so that the strap 32B circumferentiates the dimension D2 of the forearm in such a manner so as to effectively restrict that strap from riding up the wearer's arm. If desired, the straps 32A and 32B can be adjustable, and can include types of fasteners mentioned above to secure them in a customized manner around the lower arm of the wearer, with a desired amount of tension therein to hold those straps tight to the forearm. In some cases, the anti-ride up element might not be tapered.

The orthosis 10 can include adjustable lower end anchors 28A and 28P. The lower end anchor 28A can be an adjustable D-type loop or buckle that secures a portion of the primary inferior end 42, of the anterior stability strap 40 to the sleeve lower arm portion 32. Depending on where it is located, this primary inferior end also can be referred to as a primary posterior end, primary lateral end or primary anterior end. Likewise, the lower end anchor 28P can be a similar loop or buckle that secures a portion of the secondary inferior end 52 of the posterior stability strap 50 to the lower arm portion 32. Depending on where it is located, this secondary inferior end also can be referred to as a secondary posterior end, secondary lateral end or secondary anterior end. Where the orthosis includes the humeral head strap 80, the orthosis also can include adjustable lower end anchor 29 of a similar construction that secures the humeral head strap 80 to the lower arm portion 32. Optionally, the lower end anchors can include cams, sliding buckles, pins, clamps or other fasteners to selectively secure the respective ends of the straps with a desired tension force stored therein.

As mentioned above, the orthosis 10 can include anterior stability strap 40 and a posterior stability strap 50. Each of these straps can optionally be elastic and configured to store respective tension forces TF1 and TF2. The anterior stability strap 40 includes a primary anterior end, or first end, or upper end 41 and a primary posterior end, or lower end, or second end 42. Primary anterior end 41 is fixedly and permanently anchored to the shoulder portion of the base 10, generally on the base anterior 22, superior to the shoulder. The anterior stability strap 40 also includes a primary intermediate part 43 that extends between the primary anterior end and primary inferior end. Incidentally, the primary inferior end can be named according to its location where the strap terminates inferiorly, for example, the primary posterior end where it terminates on the posterior of the wearer or the base.

As mentioned above, the anterior stability strap includes the primary intermediate part 43. This part 43 extends inferiorly downward from the primary anterior end 41, over an anterior portion 30A of the sleeve or base upper portion 31. It further transitions rearward to a posterior portion 30P of the sleeve or base. The intermediate part 43 also extends over this posterior portion 30P to the primary posterior end 42 of the strap 40. This primary posterior end 42 can be disposed adjacent the posterior portion of the sleeve or base. The primary posterior end 42 also can be adjacent the posterior of a wearer, on or adjacent the lower arm at a position inferior to the elbow 103.

As shown in FIG. 12, the primary anterior end 41 and the primary posterior end 42 can be in a fixed position relative to the base, sleeve and wearer in general. These components can be constructed so that they do not move relative to those elements. The intermediate part 43 between these ends however can be configured to stretch and to store a tension force TF1 generally within the anterior stability strap, between the respective first and second ends 41, 42 or more generally between the anchors 26 and 28A.

With the configuration of the anterior stability strap, its ends and intermediate part, that component can be adjusted to establish a predetermined tension force TF1 within the intermediate part and the strap. Due to the routing of the anterior stability strap 40, the strap can be used to provide inferior and posterior support to the glenohumeral joint of the wearer. To provide adjustment, the anchor 28A can be loosened to allow the primary posterior end 42 slide or move relative to it. A wearer or a healthcare provider can pull, or otherwise extend the end 42 farther past the anchor element 28A to increase a tension force TF1 stored in the anterior stability strap. The precise preselected tension force TF1 can be selected to address the degree of instability or joint laxity in the glenohumeral joint. After the end 42 is adjusted, and the predetermined tension force TF1 achieves a desired level, for example, by changing the tension force TF1 from a first force to a second greater force, the anchor 28A can be engaged to fix the strap end at a fixed location and orientation relative to the anchor.

Optionally, during the adjustment of the tension force TF1 in the anterior stability strap 40, as well as any other straps mentioned herein, such as the posterior stability strap and the humeral head strap, the distance between the respective upper and lower anchors remains substantially static, that is, the same, even when the tension force of the respective straps are changed. In this manner, the respective upper and respective lower anchors remain in substantially the same spatial orientation relative to one another, the base and/or the sleeve throughout the adjustment. As an example, the upper end anchor 26 and the lower end anchor 28A can remain stationary relative to the wearer, and relative to one another when the preselected tension TF1 of the anterior stability strap is established and/or changed as described above.

The orthosis 10 also can include an anterior first anchor 60 fixedly and immovably joined with the anterior portion 30A of the sleeve 30 or base, generally adjacent the upper arm portion 32. As shown in FIGS. 1 and 1A, the anterior first anchor 60 can define a first anterior anchor channel 60C. This channel can be defined between an overlapping panel 60S that is joined to the underlying sleeve 30 via a fastening element 60F. As shown, the fastening element 60F can be in the form of stitching, but of course can be other fastening devices, such as glue, cement, a hot weld, fasteners or the like. Further the channel optionally can be in the form of a sheath simply stitched to the underlying panel. The anterior stability strap 40 can be slidably disposed within the channel 60C so it can freely move therein. Due to the curvature of the anterior first anchor, as shown in FIG. 1, that anchor redirects the strap 40 through it inferiorly and in a curved manner, wrapping the anterior stability strap 40 downward and behind to the posterior 30P of the sleeve or base.

Optionally, due to the slidable relationship between the anchor 60 and the anterior stability strap, that anterior stability strap can be constrained to extend and move substantially only along a permanent first fixed route so that the anterior stability strap cannot be rerouted along a different route over the shoulder. For example, as shown in FIG. 1, the anterior stability strap 40 can extend along fixed route or pathway FR1. Generally, due to the constraints of the intermediate part 43 by the anchor 60 and the ends by the anchors 26 and 28A, this strap cannot move or slide across the sleeve and/or base or generally across the shoulder of a wearer to deviate from this first fixed route FR1. With this type of fixed routing, the anterior stability strap can be fixed desired route by the manufacturer of the orthosis. Optionally, that route is configured so that it cannot be changed by a later user or a wearer of the orthosis. In turn, this can reduce the complexity of the orthosis and its operation for users and wearers. Further optionally, the only adjustment the user can make is adjustment of the tension forces in the anterior stability strap or other straps as described further below. The user in this case need not be concerned with the particular routing of the stability straps over the shoulder, relative to the glenohumeral joint.

Figure 5:
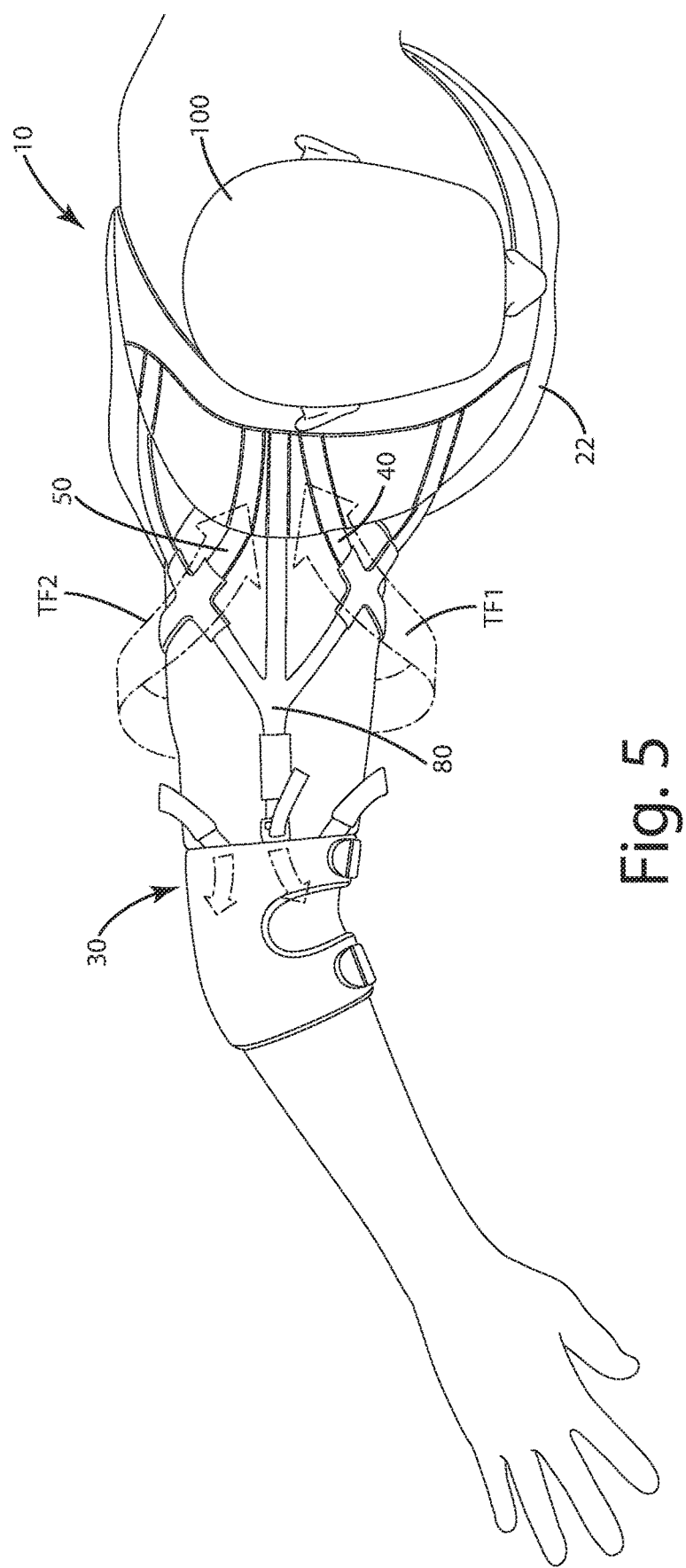
FIG. 5 is a top view of the shoulder brace in a tensioning mode to address anterior, inferior and posterior instability of the glenohumeral joint.
Figure 6:
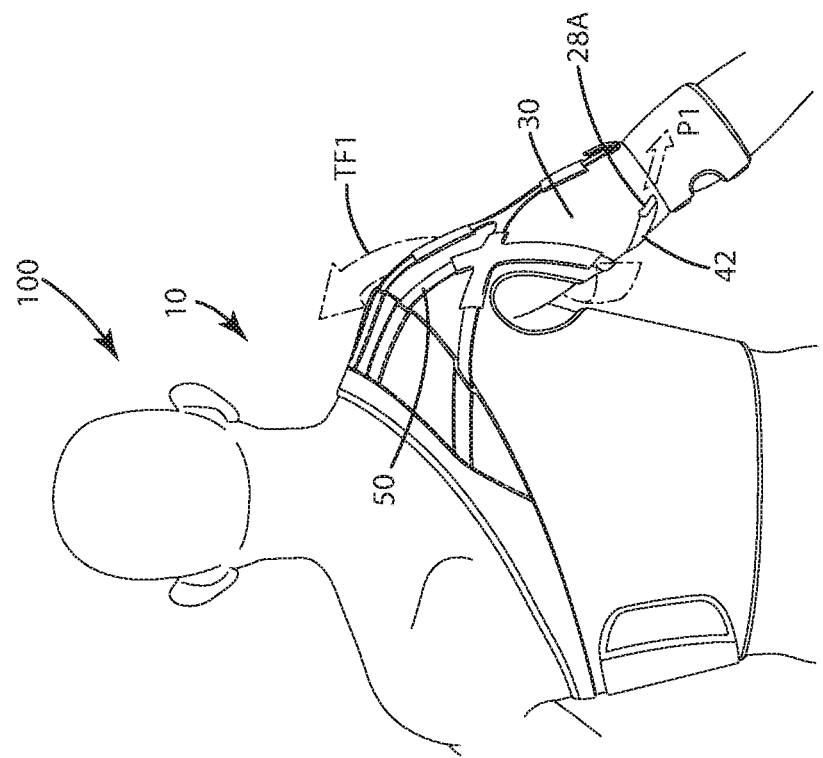
FIG. 6 is a front view of the shoulder brace with an anterior strap in a tensioning mode to address inferior and posterior instability of the glenohumeral joint.
Figure 7:
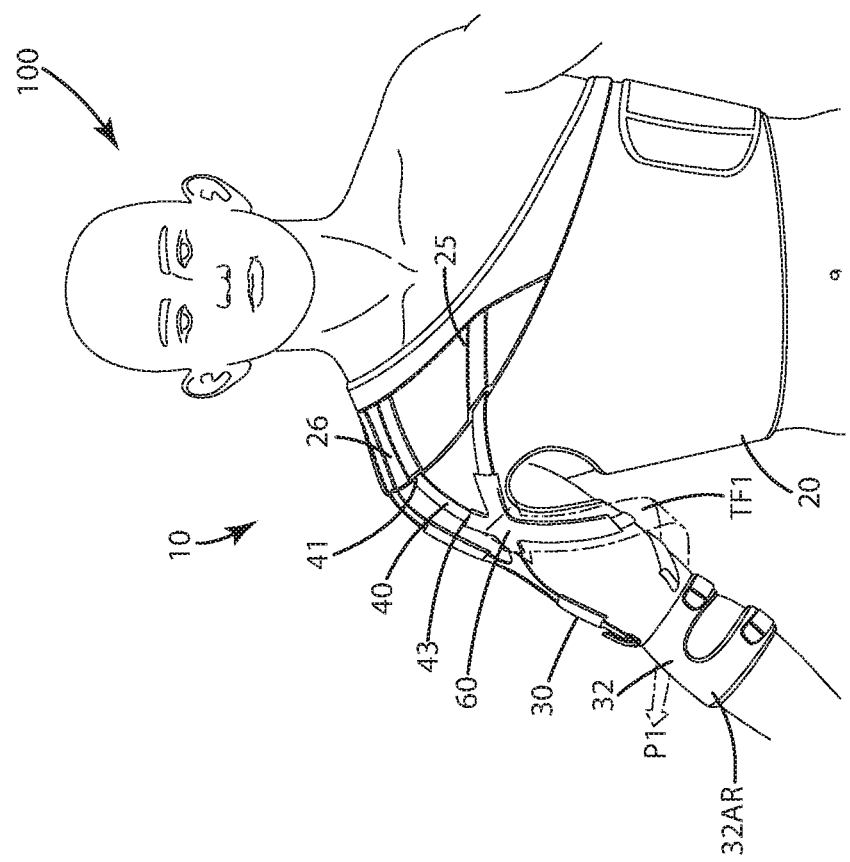
FIG. 7 is a rear view of the shoulder brace with an anterior strap in a tensioning mode to address inferior and posterior instability of the glenohumeral joint.

Operation of the anterior stability strap 40 can be understood with reference to FIGS. 5-7. As shown there, the orthosis 10 is installed on a wearer 100. The anterior stability strap 40 is placed in an adjustment mode. A user loosens the lower anchor element 28A and can grasp a portion of the primary posterior end or lower end of the anterior stability strap 40. The user can exert a force P1 to pull the end 42 under force. Because the strap, in particular the intermediate part 43, is constrained by the anterior anchor element 60 with its channel 60C, the stability strap 40 does not move relative to the shoulder, the sleeve and the like during the pulling. The anterior end 41 also remains static relative to the anchor 26. The bolster element 25 also can prevent the tension force TF1 exerted within the stability strap 40 from pulling the base and/or sleeve inferiorly. After the user determines that the first tension force TF1 in the stability strap is appropriate to address the instability in the wearer's shoulder or glenohumeral joint, the user can adjust the anchor 28A to fix the end 42 to the lower arm portion. When this occurs, the strap exerts the stored tension force TF1 on the lower arm portion and/or anti-ride up element 32AR. Because of the securement of the anti-ride up element to the lower arm of a wearer, the element does not move, so the tension force is transferred to the arm and shoulder and glenohumeral joint of the wearer. As a result, the tension force TF1 in the strap operates to provide inferior and posterior support to the glenohumeral joint of the wearer.

As mentioned above, the orthosis 10 also can include a posterior stability strap 50. This posterior stability strap 50 can include a posterior or upper end 51 and a lower or second inferior end 52 as shown in FIGS. 1 and 2. Between these ends an intermediate part 53 is disposed. The ends 51 and 52 can be anchored to the base with anchors 27 and 28P, similar to the anchor 26 and 28A described in conjunction with the anterior stability strap 40. The second end 52 also can be joined with the sleeve lower arm portion 32 on the inferior portion 30A of the sleeve using an anchor similar to the anchor 28A. This anchor 28P for the posterior stability strap can also be adjustable like the anterior stability strap above. In addition, the posterior strap can be guided by a posterior first anchor 70, similar or identical to the anterior first anchor 60 described above. The posterior first anchor 70 can be fixedly and permanently joined with the posterior 30P of the sleeve or base. The posterior first anchor can define a first posterior anchor channel 70C as shown in FIG. 2A. This channel 70C can also traverse or be in communication with a channel of a posterior humeral head anchor 88. Optionally, the first anterior anchor channel 60C, likewise can be contiguous with and/or overlap the anterior anchor channel of a humeral head anterior anchor 80CA. The respective posterior and anterior humeral head anchors can be constructed similarly to the posterior first anchor and the anterior first anchor as described above.

As shown in FIGS. 2 and 2A, the secondary intermediate part 53 of the posterior stability strap 50 can be slidably disposed in the first posterior anchor channel on the posterior portion 30P of the sleeve 31 generally in the upper arm portion. The posterior stability strap 50 can be joined and fixedly anchored to the base posterior 24, superior to the shoulder. The posterior stability strap 50 also can include as mentioned above the secondary intermediate part 53 that extends inferiorly downward from the secondary posterior end 51, or the upper end of the strap. The secondary intermediate part 53 can extend over the posterior portion 30P of the sleeve or base upper portion 31. From there it can transition forward, wrapping around the arm, to an anterior portion 30A of the sleeve 30. The secondary anterior end 52 can be selectively joined with the sleeve 30 via the anchor 28P so that the preselected tension force TF2 and the secondary anchor strap 28P can be adjusted. With this selective adjustment of the tension force TF2, a user can provide anterior and/or inferior support to the glenohumeral joint of the wearer 100.

As can be appreciated from FIGS. 1 and 2, the intermediate parts 53 and 43 of the respective posterior stability strap and anterior stability strap can crisscross or otherwise traverse one another on the medial side of the wearer's arm, and in particular the medial side of the wearer's upper arm 107. If desired, these intermediate parts can be enclosed in a sheath to reduce friction therebetween. Otherwise, they can be free floating over one another, depending on the application.

Operation of the posterior stability strap 50 can be understood with reference to FIGS. 5, 8 and 9. As shown there, the orthosis 10 is installed on a wearer 10. The posterior stability strap 50 is placed in an adjustment mode. The user loosens the lower anchor element 28P and can grasp a portion of the secondary interior and/or lower end 52 of the posterior stability strap 50. The user can exert a force P2 to pull the end 52 under force. Because the strap, in particular the intermediate part 53, is constrained by the posterior anchor element with its respective channel, the stability strap 50 does not move relative to the shoulder, the sleeve or the wearer in general. The upper or secondary posterior end 51 also remains static relative to the anchor 27. The bolster element 25 also can prevent the tension force TF2 exerted within the stability strap 50 from pulling the base and/or sleeve inferiorly. After the user determines that the second tension force TF2 in the stability strap 50 is appropriate to address the instability in the wearer's shoulder or glenohumeral joint, the user can adjust the anchor 28P to fix the end 52 to the lower arm portion and the sleeve 30 in general. When this occurs, the strap exerts a stored tension force TF2 on the lower arm portion and/or the anti-ride up element 32AR. Because of the securement of the anti-ride up element to the lower arm of the wearer, the element does not move, and thus the forces are transferred to the arm, shoulder and glenohumeral joint of the wearer. As a result, the tension force in the posterior stability strap operates to provide anterior and/or inferior support to the glenohumeral joint of the wearer. In addition, the posterior strap provides proprioceptive feedback to the wearer so that the wearer can feel when the arm is rotated externally to a position that could compromise the glenohumeral joint and previous surgical repairs relative thereto.

Optionally, the orthosis 10, as shown in FIGS. 3, 4, 10 and 11 can include a humeral head stability strap 80. This strap can be under tension forces TF3A, TF3B, TF3C to effectively pull the humeral head into the glenohumeral joint. In turn, this can provide inferior and multidirectional support to the glenohumeral joint 105G of the wearer. The humeral head stability strap 80 can include a first humeral head stability strap 80A having a first upper end 81A that is fixedly and permanently anchored to the shoulder portion of the base between the anterior of the base 22 and the posterior of the base 24. This upper end 81A also can be anchored superior to the shoulder. The first humeral head stability strap 80A can include a first intermediate part 83 that extends inferiorly downward from the first upper end, over a lateral side of the sleeve upper portion 31. The intermediate part 83 can transition to an inferior portion of the sleeve, downward toward the elbow. The first humeral head stability strap can include a first lower end 82 that is selectively joined with the sleeve 30 so that as described further below, preselected tension TF3A can be exerted in the strap 80A via adjustment of the same. The first humeral head stability strap 80A can be guided by one or more lateral anchors 83A and 84A similar to those described above. These lateral anchors can be fixedly and immovably and/or permanently joined with a lateral portion of the sleeve and can define anchor channel similar to those described above in connection with the other stability straps. The intermediate part 83 of the humeral head strap can be slidably disposed in lateral anchor channels of these anchors on a lateral portion of the sleeve. This can ensure that the strap is guided over the lateral portion of the shoulder in a consistent and precise manner. The lower end 82 can be fixed using an anchor 29 similar to the anchors 28A and 28P described above for adjustment of the end 82 relative thereto.

Figure 3:
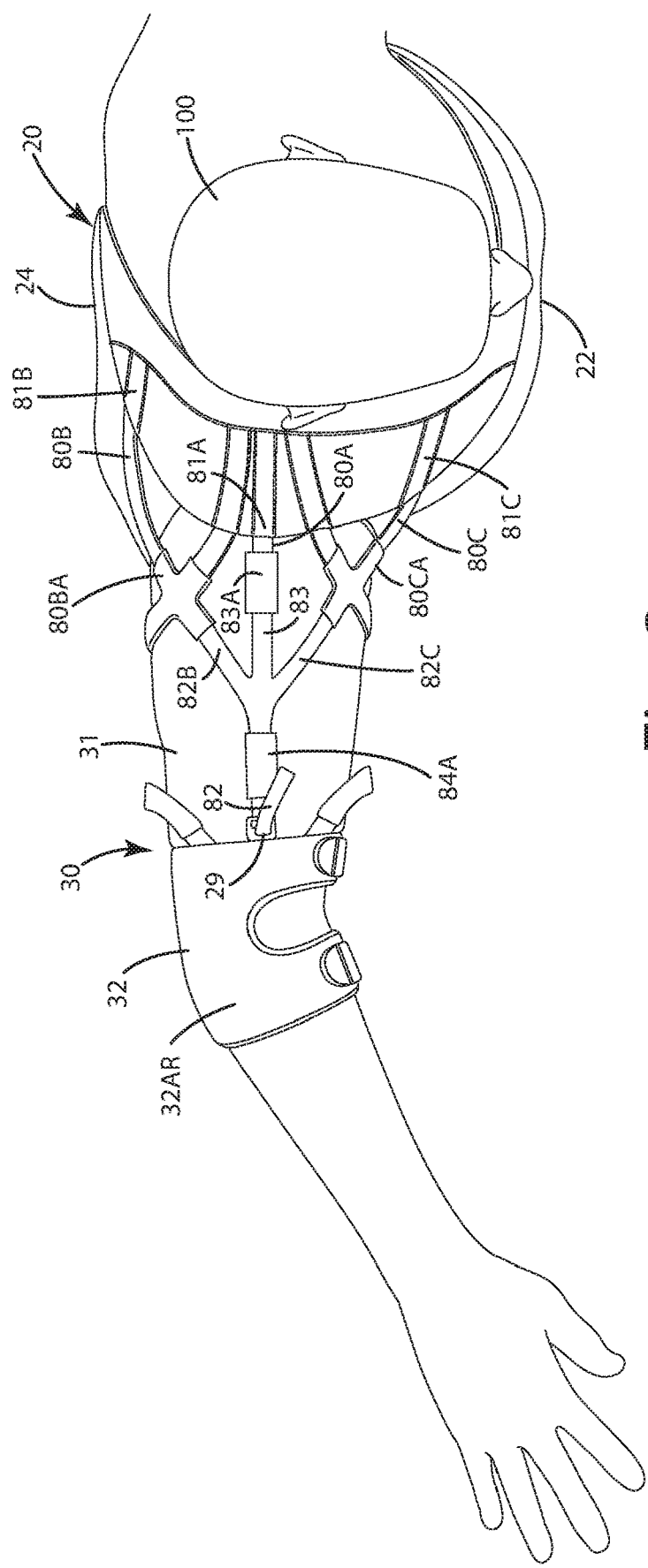
FIG. 3 is a top view of the shoulder brace in a static mode.
Figure 4:
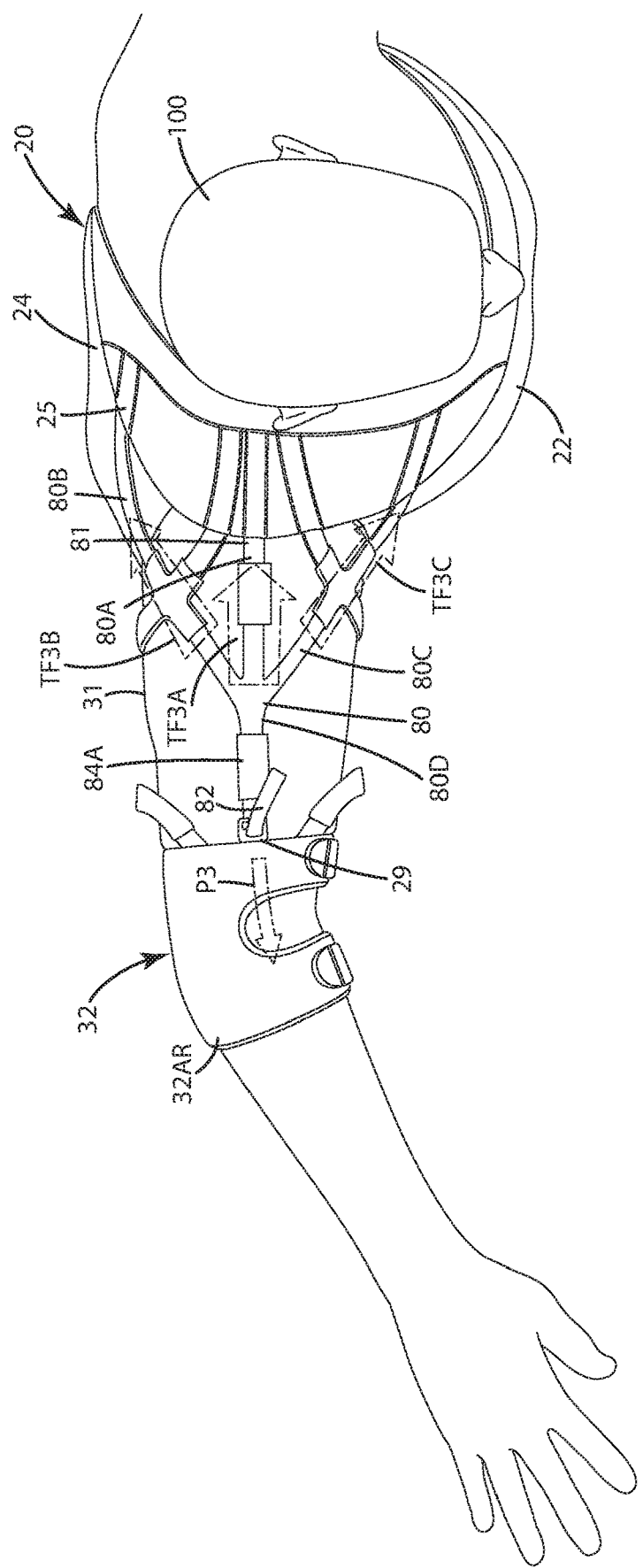
FIG. 4 is a top view of the shoulder brace in a tensioning mode to pull a humeral head of the wearer into a glenohumeral joint.

Optionally, the humeral head stability strap can include a second humeral head stability strap 80B and a third humeral head stability strap 80C. The second humeral head stability strap 80B can be disposed across at least a portion of the posterior 24 of the base 20. The third humeral head stability strap can be disposed across at least a portion of the anterior 42 of the base 20. The second strap 80B can include a second upper end 81B and a second lower end 82B. The first upper end to be fixedly and permanently anchored to the shoulder portion of the base on the base posterior 24. The second lower end can be joined with the first intermediate part 83 of the first humeral head stability strap. The third humeral head stability strap can include upper end 81C fixedly and permanently anchored to the shoulder portion of the base on the anterior of the base, superior to the shoulder. The third lower end 82C can be joined with the first intermediate part 83 of the first humeral head stability strap. In effect, the second and third head stability straps can be configured to evenly provide tension across the anterior and posterior of the base. Optionally, the first, second and third humeral straps can be configured to form a "W" shape, as shown in FIGS. 3 and 4 from a top view across the top of the shoulder of the wearer. Similar to the anterior posterior stability strap routes noted above, the routing of the first, second and third humeral straps is substantially constant. With the anchors, the respective humeral head stability straps are configured to not slide around or change orientation relative to the sleeve and/or the base.

Further optionally, the respective second and third head stability straps can also be guided by posterior anchors 80BA and anterior anchors 80CA, which include channels, like those described above, to guide the respective straps.

Operation of the humeral head stability straps is illustrated in FIGS. 4, 10 and 11. There, a user can adjust the anchor 29 and manipulate the end 82 of the strap, optionally pulling on it with force P3 until forces TF3A, TF3B and TF3C achieve a desired level to address inferior and multidirectional instability and provide corresponding support to the glenohumeral joint of the wearer. During the adjustment, the respective humeral head straps travel along their fixed routes, constrained by the respective anchors 83A, 84A, 80BA and 80CA. Thus, upon the pulling, primarily only the tension is adjusted in the respective humeral head straps rather than position or orientation of those straps. After the adjustment is complete, the anchor 29 is secured and the tension forces are stored in the respective straps to provide the desired support.

In the orthosis of the current embodiments, the stability straps optionally are automatically aligned with designated, fixed tension force pathways upon donning the brace to address respective anterior, posterior, multidirectional instabilities. With this embodiment, one might only tighten the straps to apply the desired tension therein, rather than reorient the straps relative to the sleeve and/or the base or the anatomy of the wearer.

Figure 14:
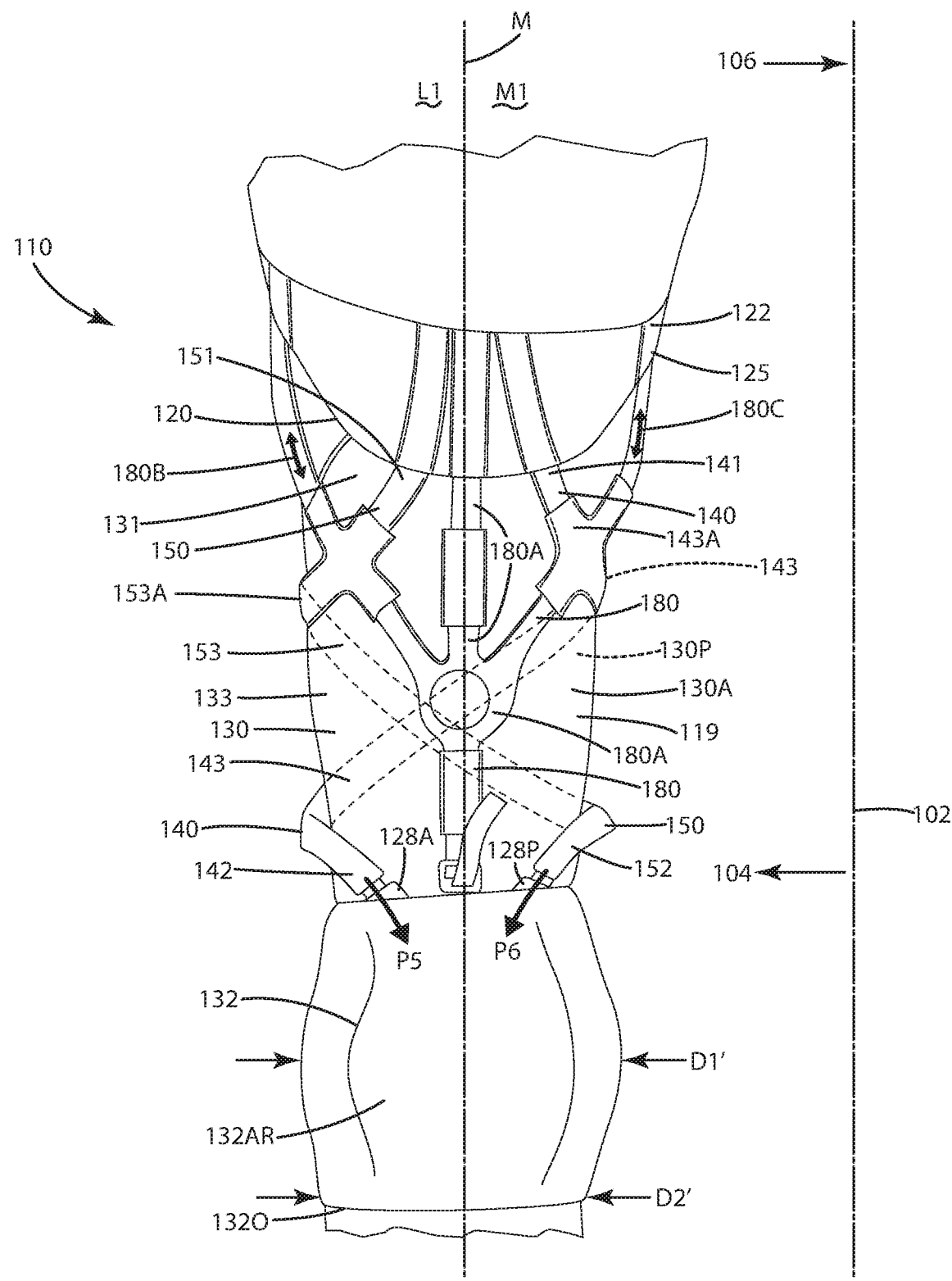
FIG. 14 is a front view of a first alternative embodiment of the orthosis in the form of a knee brace.

A first alternative embodiment of the orthosis is shown in FIG. 14 and generally designated 110. This embodiment is similar in structure, function and operation to the current embodiment described above in connection with the shoulder brace with several exceptions. For example, the knee brace 110 can include a base 120 having a sleeve 130. The sleeve can include a sleeve upper portion 131 and a sleeve lower portion 132. The sleeve also can include a base anterior 130A and a base posterior 130P. The sleeve upper portion can be configured to extend over an upper portion or upper leg of a wearer, for example over the quadriceps and hamstrings of the wearer. The sleeve upper portion 131 also can extend superior to a joint of the wearer, for example the knee joint 119. The sleeve central portion 133 can extend over the joint, for example the knee joint. The sleeve lower portion 132 can include an anti-ride up element 132AR and can terminate at an opening 132O configured to receive a portion of a wearer's appendage inferior to the knee. Anti-ride up element 132AR can be tapered along a length extending away from the knee and/or upper portion.

Optionally anti-ride up element can include a first dimension D1' adjacent the knee and/or upper portion. The first dimension D1' can be greater than a second dimension D2' of the anti-ride up element adjacent the opening 132A. In this manner, the anti-ride up element can prevent the sleeve from riding up the leg and knee of a wearer from an inferior position to a superior position along the leg.

The orthosis 110 can include a first stability strap 140 having a first upper end 141 that is fixedly and permanently anchored to the base and optionally the base anterior 122 in a location superior to the sleeve central portion 133. The first upper end 141 can be on the medial side of the midline M. The strap can include a first intermediate part 143 extending downward from the first upper end adjacent the base anterior on a first side M1 of a midline M of the leg. Optionally the first side M1 can be the medial side of the leg. The first intermediate part 143 can extend over the central portion in transition rearward to the base or sleeve posterior 130P, traversing to a second opposing side or lateral side L1 of the midline M. The intermediate part can extend over the base posterior 130P to the first lower end 142 which can be disposed on the lateral side L1 of the midline. The first lower end can be selectively joined via the anchor 128A to the sleeve below the knee joint 119.

The orthosis can include a second stability strap 150 having a first upper end 151 that is fixedly and permanently anchored to the base, optionally on the base anterior 130A end locations. The sleeve central portion 133 and the strap first end can be located on the lateral side L1 of the midline M strap can include a first intermediate part 153 that extends inferiorly downward from the first upper end adjacent the base on a second side or lateral side L1 of the midline M of the leg. The first intermediate part 153 can extend or the central portion in transition rearward to the base or sleeve posterior 130P, traversing to a second opposing or medial side M1 of the midline M. The intermediate part can extend over the base posterior 130P to the first lower end 152 which can be disposed on the medial side M1 of the midline. The first lower end can be securely joined via the anchor 128P to the sleeve below the knee.

This embodiment also can include first and second anchors 143A and 153A fixedly and immovably or permanently joined with the base, for example the interior of the base. The anchors can define anchor channels in the respective intermediate parts of the first and second stability straps slidably disposed in the respective anchor channels of the respective sides of the midline M as shown in FIG. 14. Optionally, the first and second stability straps can traverse one another over the base posterior 130P or some other portion of the base or sleeve.

In this embodiment, the orthosis 110 also can include a bolster element 125 that is constructed from a flexible material that is more rigid than the base. Bolster element can be joined with the base anterior 130. One or more anchors can be joined with the bolster element to join the respective stability straps thereto. The bolster element can prevent bunching of the base and the sleeve due to the preselected tension in the respective first and second stability straps.

This embodiment can optionally include a patella strap 180 which can join the upper and lower ends, the respective upper bolster element 125 and the lower leg portion 132 and/or anti-ride up element of the sleeve. This patella strap 180 also can be configured to define an aperture 180A that centers the patella therein. Due to the configuration of the upper straps 180A, 180B and 180C, the patella strap can provide constant, consistent and even forces on the patella to keep it in a desired location and tracking properly.

A second alternative embodiment of the orthosis is shown in FIGS. 15-19 and generally designated 210. This embodiment is similar in structure, function and operation to the shoulder brace embodiment described above with several exceptions. For example, the shoulder brace 210 can include a base 220 having a sleeve 230. The sleeve can include a sleeve upper portion 231 and a sleeve lower portion 232, with a central portion 233 therebetween. The sleeve also can include a sleeve or base anterior 230A and a sleeve or base posterior 230P. The sleeve upper portion 231 and/or the sleeve central portion 233 can be configured to extend over a shoulder and in particular a glenohumeral joint 105G of the subject 100. The sleeve upper portion 231 also can extend inferiorly downward from the glenohumeral joint to and optionally past the elbow 103. The sleeve lower portion 232 can include an anti-ride up element 232AR and can terminate at an opening 232O configured to receive a portion of a wearer's appendage inferior to the elbow. The anti-ride up element 232AR can be tapered along a length extending away from the elbow along the forearm, and constructed virtually identical to the anti-ride up element in the embodiments above.

The base 220 of this brace 210 can be constructed slightly different from the shoulder brace embodiment described above. For example, the base 220 can include a closure system 220C which can be in the form of a quick release buckle and/or a string set which can be laced up to tighten and close the closure, thereby securing the base to the torso. The base also can include a belt 220B that extends forwardly from the base posterior to 230P and includes a belt closure 220BC across the chest or generally anterior to the torso of the wearer 100. The belt closure 220BC can be a simple hook and loop fastener, a buckle, or another type of fastening mechanism. The belt 220B also can include optional grippy material, such as strips of silicone or rubber on the interior, facing the subject's body, to provide extra grip and to prevent excessive movement of the base 220 relative to the torso.

The sleeve 230 can be constructed slightly different from the sleeve in the shoulder brace embodiment above. The sleeve in this embodiment can be integral with and/or separable from the base. The sleeve can include multiple channels which effectively operate as anchors to hold the straps adjacent the sleeve and constrain longitudinal movement of the straps, as will be described in further detail below. The channels for the respective straps can route those straps along respective predetermined, fixed routes to provide anterior, posterior, lateral and/or general stability to the glenohumeral joint.

Figure 15:
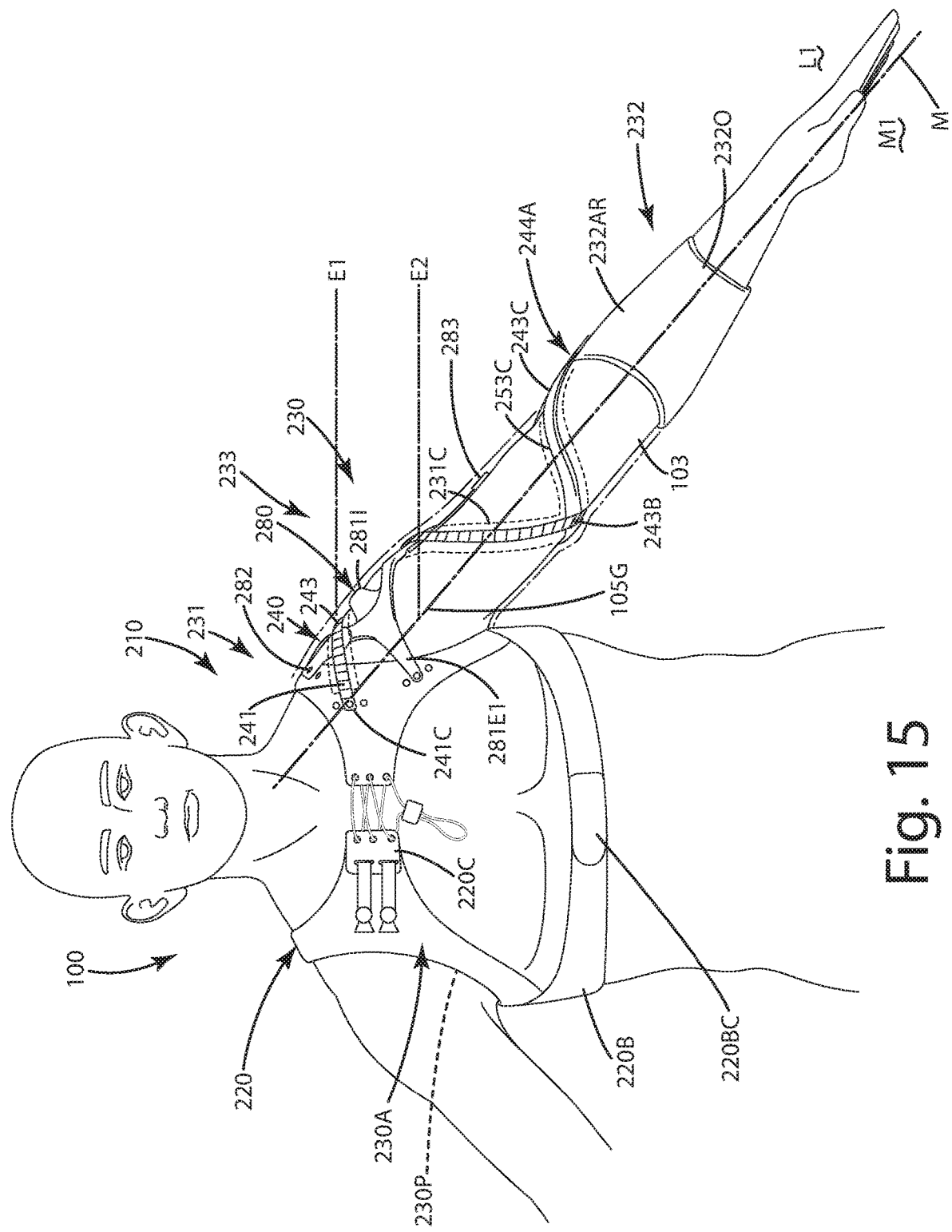
FIG. 15 is a front perspective view of a second alternative embodiment of the orthosis in the form of a shoulder brace, the orthosis having a shoulder compression mitt integrated with a sleeve.
Figure 16:
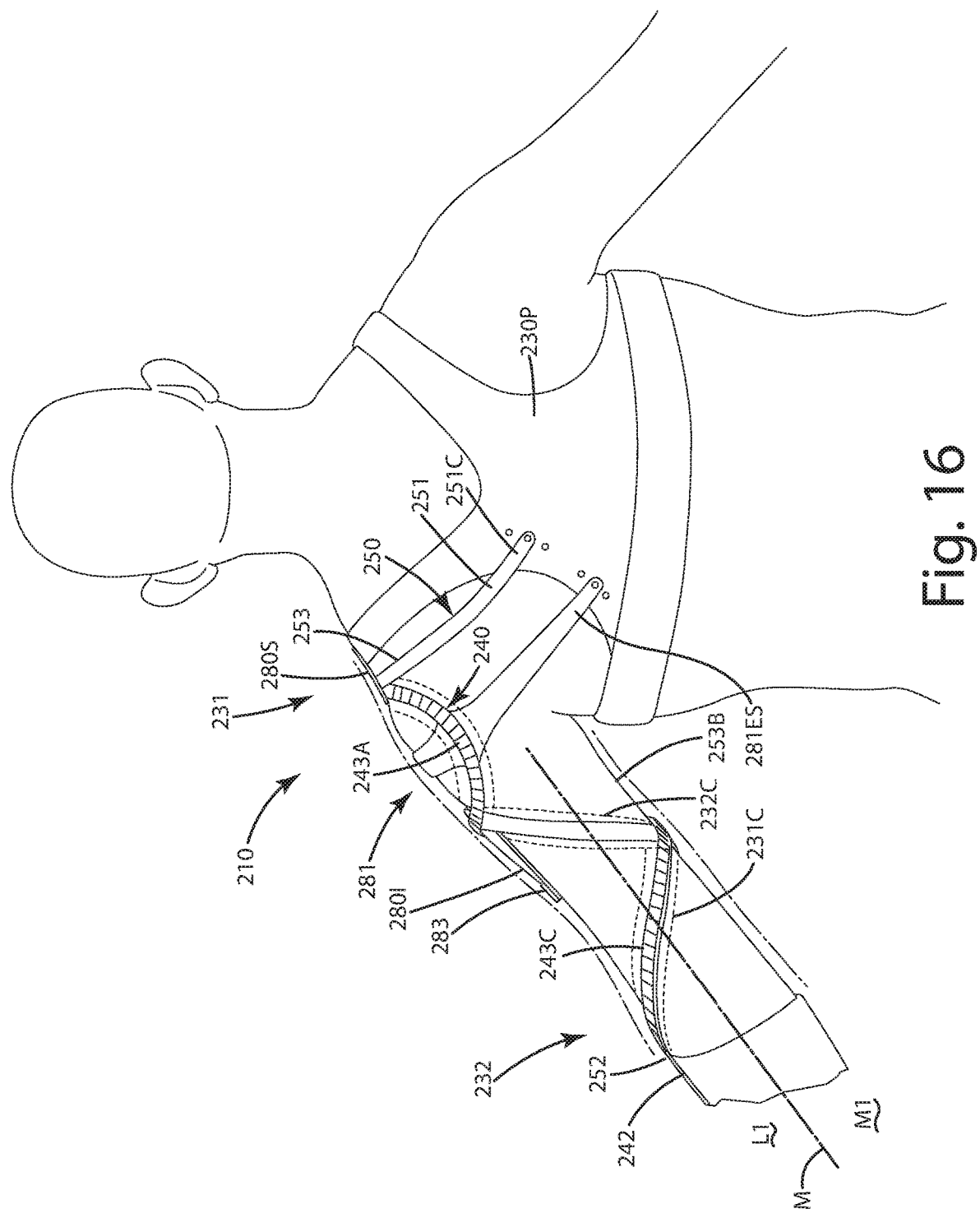
FIG. 16 is a rear perspective view of thereof.
Figure 19:
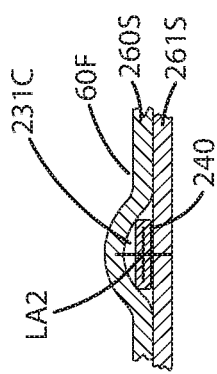
FIG. 19 is a section view taken along lines 19-19 of FIG. 17 showing an exemplary strap in a channel.
Figure 18:
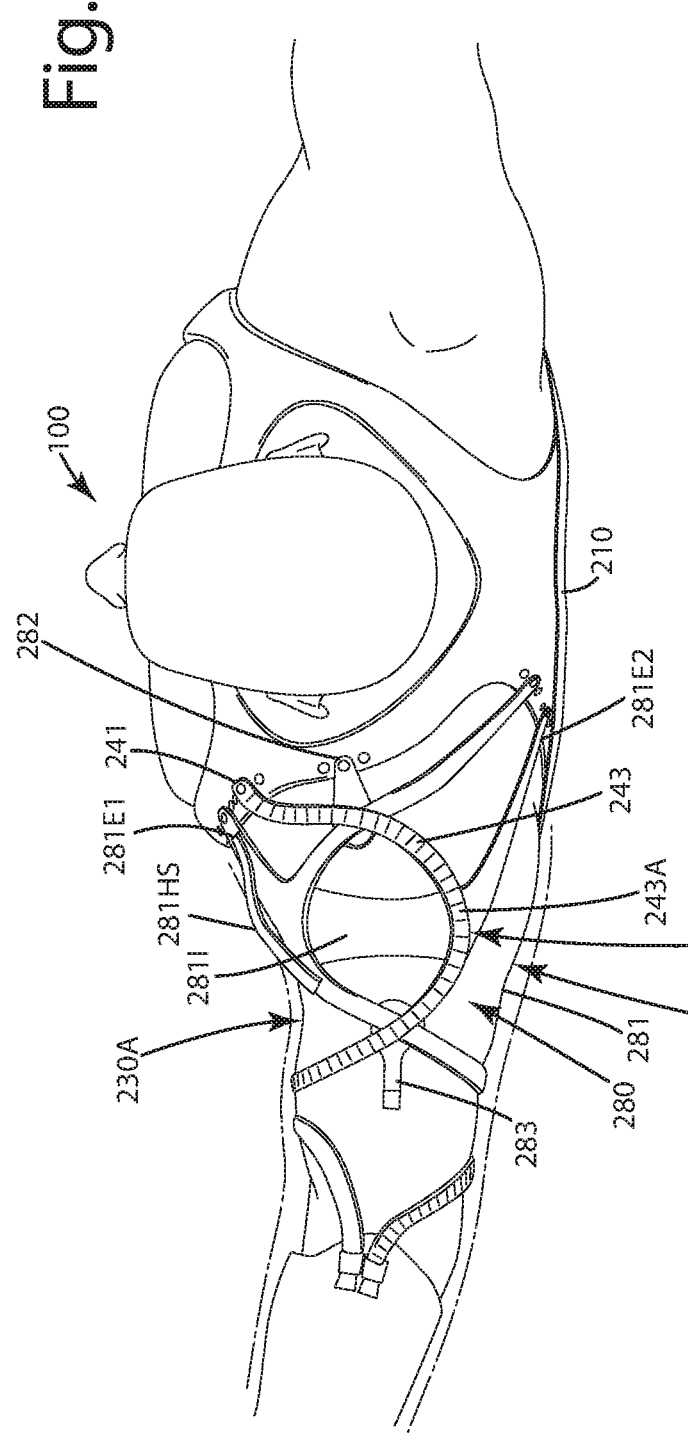
FIG. 18 is a top view thereof.
Figure 20:
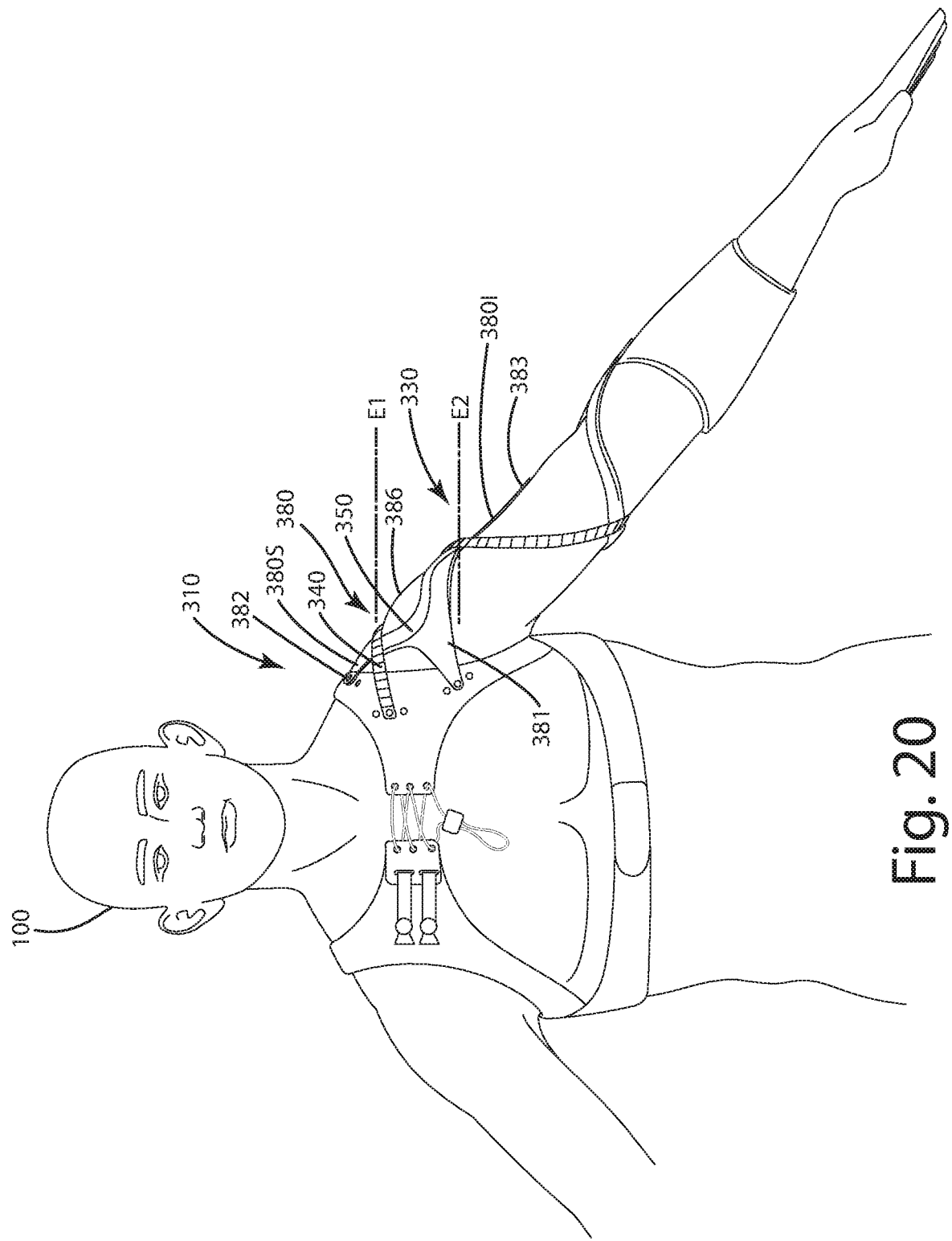
FIG. 20 is a front perspective view of a third alternative embodiment of the orthosis in the form of a shoulder brace, the orthosis having a modular shoulder compression mitt.
Figure 21:
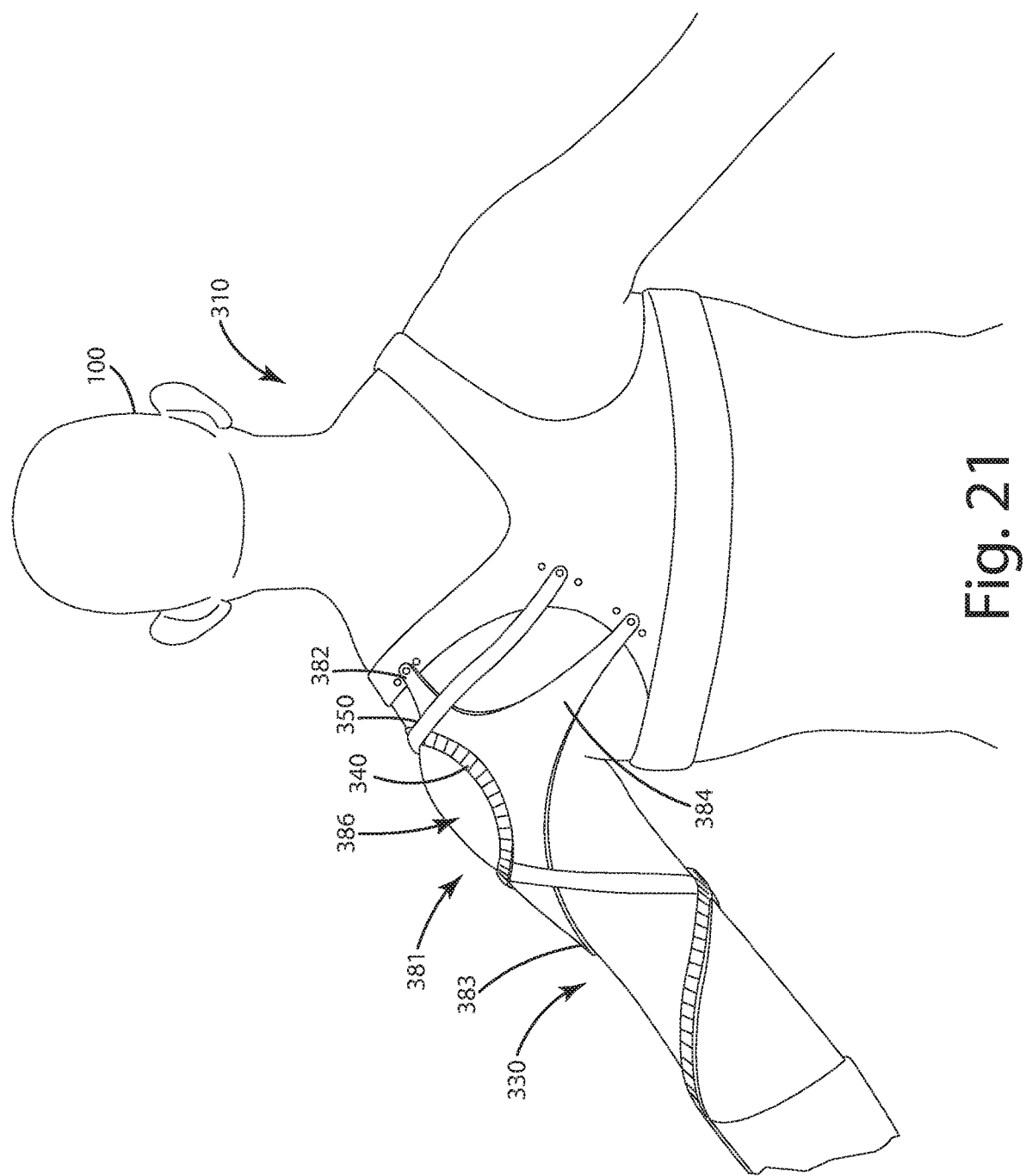
FIG. 21 is a rear perspective view of thereof.

With reference to FIGS. 15-16, more particularly, the sleeve 230 can define a first channel 231C that can accommodate an anterior stability strap 240, and a second channel 232C that can accommodate a posterior stability strap 250. The first channel 231C and the second channel 232C can be similar to one another and so too can any other respective channels in the sleeve. An exemplary first channel 231C is illustrated in FIG. 19. There, the channel 231C is defined between a secondary layer to 260S that is glued, knitted, welded, cemented or otherwise joined with a primary layer 261S. These two layers can be constructed from woven or knitted fabrics, plastics, or other suitable substrates as described in connection with the embodiments above. The channel 231C, within which the anterior strap 240 is slidably disposed, can be a void between the layers 260S and 261S that is sized to accommodate that strap. The channel 231C operates to constrain movement such that the strap 240 can slide longitudinally along a longitudinal path LA2 of the respective channel 231C. Generally, the strap is constrained by the channel along this longitudinal path LA2 such that the strap does not move significantly laterally outside the channel and over different portions of the appendage to which the sleeve is attached. Again this can constrain the strap to be able to move, for example slide, primarily longitudinally through the channel, but without moving laterally or otherwise across the shoulder joint and/or arm. Thus, the strap is constrained to a predetermined fixed route. It will be appreciated that the second channel 232C, and any other channels that construct straps herein can be similar in structure and function.

Optionally, the respective channels can be outfitted with a covering, stiffening agent or low friction materials to enhance sliding and/or movement of the respective straps within. Further optionally, while a strap is configured to slide within the channel, that strap need not necessarily slide throughout the entire channel. For example, certain portions of the strap can be stitched or secured to the primary or secondary layers so that they are generally immovable, while other portions are not stitched or secured, and generally are able to move via a sliding action.

The channels 231C, 232C can be outfitted along fixed routes that are different from the routes of the embodiment of the shoulder brace above, but that generally correspond to the routes of the respective anterior 240 and posterior 250 stability straps. Therefore, the routes of those straps 240, 250 can be substantially identical to the routes of the respective channels of the sleeve or base. Accordingly, the description of the routes of the stability 240 and 250, straps below as well as any other straps herein, will be understood to be the same as the routes of their respective channels.

As mentioned above, the orthosis 210 can include anterior stability strap 240 and a posterior stability strap 250. Each of these straps can optionally be elastic and configured to store respective tension forces, similar to the tension forces TF1 and TF2 as described in connection with the shoulder brace embodiment above. These tension forces, the reactions and the adjustments to all straps in this embodiment is similar to the same in the shoulder brace embodiment above, so will not be described again in detail here.

The anterior stability strap 240 includes a primary anterior end, or first end, or upper end 241 and a primary inferior end, or lower end, or second end 242. Primary anterior end 241 is anchored to the shoulder portion of the base 210, optionally on the base anterior 230A, superior to the shoulder. In this embodiment, the primary anterior end 241 can be mounted via a connector 241C, which in some cases can be referred to as a first anchor. This connector 241C can include male and female connectors that interlock with one another to provide superior and inferior adjustment capabilities for the anterior stability strap relative to the base anterior 230A. In turn, this can provide satisfactory adjustment to fit a particular wearer. These male and female connectors can be holes defined in a portion of the base, with a corresponding hook or locking element associated with the end of the anterior strap that fit within the holes. A user can self-adjust the primary anterior end to place it in a suitable location simply by placing the male connector in the different respective female connectors. The connectors can be any of a variety of different mechanisms to provide the superior and inferior adjustment of the location of attachment of the strap 240 to the sleeve anterior 230A.

Figure 17:
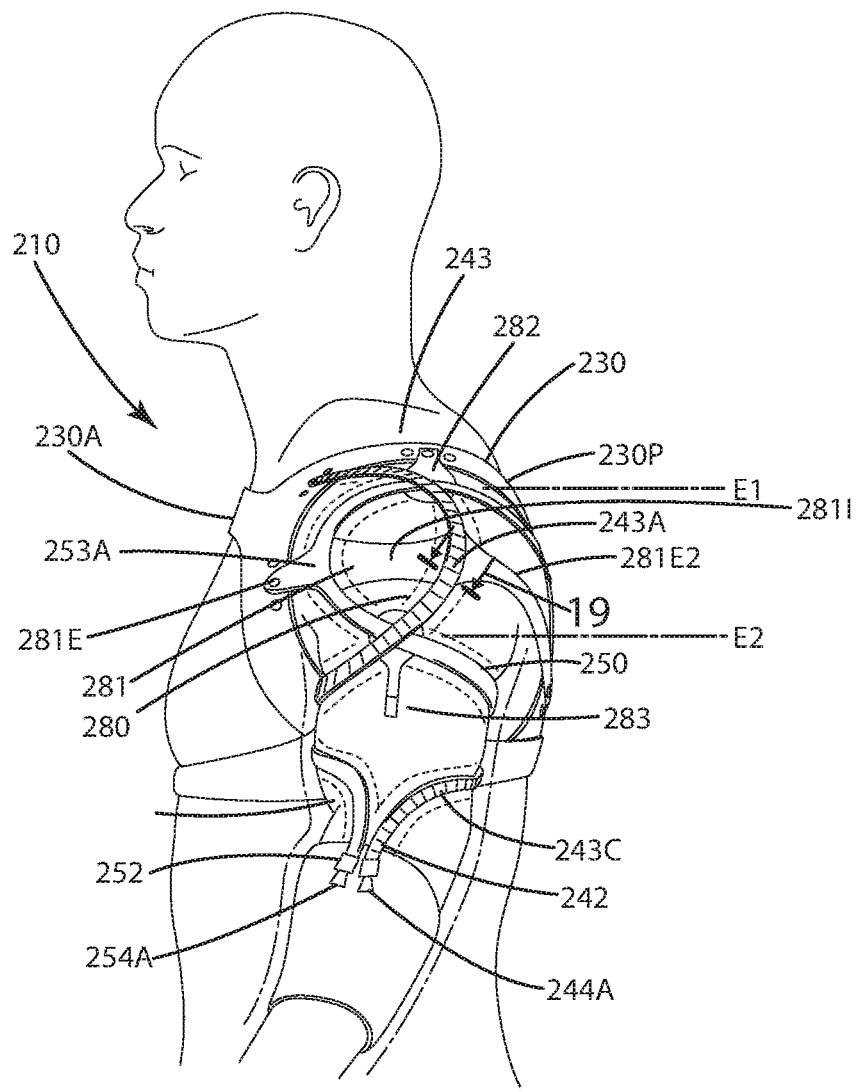
FIG. 17 is a side view thereof.

The anterior stability strap 240 can include a primary intermediate part 243 that extends between the primary anterior end 241 and primary inferior end 242. Incidentally, the primary inferior end can be named according to its location where the strap terminates inferiorly, for example, it can be called a primary posterior end where it terminates on the posterior of the wearer or the base, or it can be called a primary lateral end where it terminates on the lateral side L1 of the arm as shown in FIG. 17. Optionally, the anterior stability strap can extend at least 180° around the wearer's arm, and as shown, can extend at least 360° around the wearer's arm.

The primary intermediate part 243 can extend laterally from the primary anterior end 241, where the strap can originate, over an anterior portion 230A of the sleeve or base upper portion 231. It further transitions rearward to a posterior portion 230P of the base or the upper portion 231 of the sleeve. The intermediate part 243 can extend laterally over the glenohumeral joint 105G, crossing the joint at a first elevation E1 as the part extends toward the posterior 230P of the base. The intermediate part 243 can include a first intermediate part 243A that extends along a portion of the posterior 230P of the sleeve and/or the base before extending forward again, optionally in a curved manner, toward the anterior of the sleeve and/or base and generally the midline M of the arm. This first intermediate part 243A can be disposed on the lateral L1 side of the midline M of the arm, which generally bisects the arm into lateral and medial portions. The first end 241 can be on a portion of the medial side M1, but optionally extends onto the lateral side L1 to the extent the arm midline M is relevant in the location where the anterior end is located.

Returning to the first intermediate part 243A, it transitions forward over the biceps of the wearer 100, crossing the midline M of the arm and thus traversing a portion of the anterior 230A of the sleeve or base. The anterior strap 240 in this location reroutes to extend anteriorly forward, back across the glenohumeral joint 105G, and slightly inferior to it. The anterior strap in this location also can be disposed at a second lower elevation E2, which is inferior to the first elevation E1. These elevations can be taken relative to the coronal plane of the wearer. The second elevation E2 can be lower than the first elevation E1 by at least 1 inch, at least 2 inches, at least 3 inches, at least 4 inches, at least 5 inches or more depending on the anatomy of the wearer.

As shown in FIG. 17, the first intermediate part 243A can transition to a second intermediate part 243B, which can be disposed on the medial M1 side of the midline M of the arm on the anterior portion 230A of the sleeve. The second intermediate part 243B can wind around and under the wearer's arm to the posterior 230P of the sleeve. In so doing, it can transition to a third intermediate part 243C which can extend forward, toward the midline M as as well as the lateral portion of the wearers forearm.

The third intermediate part 243C can extend to the primary inferior end 242, which as shown, can extend to the lateral portion of the sleeve on the lateral side L1 of the midline M. There, the anterior stability strap 240 can engage a second anchor 244A that is associated with and/or joined with the anti-ride up element 232AR, which is secured to the wearers forearm, generally inferior to the elbow 103. This anterior stability strap 240 can provide posterior support and also anterior/inferior support.

The second anchor 244A can be in the form of a buckle, a cam, a hook and loop fastener, or other mechanism that selectively engages the anterior stability strap. This mechanism can enable a user to pull an excess portion of the strap beyond the anchor and thereby adjust the tension within the anterior stability strap as described above in connection with the shoulder brace embodiment above. It also can enable the primary inferior end to be adjustably joined with the sleeve so that a preselected tension in the anterior stability strap can be adjusted. As mentioned above, the first channel of the sleeve can follow a virtually identical path as that described above in connection with the anterior stability strap and its different components.

Optionally, similar to the shoulder brace embodiment above, the intermediate part 243 between the strap ends 241, 242 can be configured to stretch and to store a tension force generally within the anterior stability strap, between these respective first and second ends 241, 242.

As shown in FIGS. 15-18, the orthosis 210 also can include the posterior stability strap 250. This strap can have a secondary posterior end, or first end, or upper end 251 and a secondary inferior end, or lower end, or second end 252. The secondary posterior end 251 can be anchored to the shoulder portion of the base 210, generally on the base posterior 230P, superior to the shoulder. The secondary posterior end 251 can be mounted via a connector 251C, which can in some cases be referred to as a first anchor. This connector 251C can be similar to the connector 241C associated with the anterior stability strap 240, and therefore will not be described again here.

The posterior stability strap 250 can include a secondary intermediate part 253 that extends between the secondary anterior end 251 and secondary inferior end 252. Incidentally, the secondary inferior end can be named according to its location where the strap terminates inferiorly, for example, it can be called the secondary posterior end where it terminates on the posterior of the base or sleeve, or it can be called the secondary lateral end where it terminates on the lateral side of the arm as shown in FIG. 17. Optionally, the posterior stability strap can extend at least 180° around the wearer's arm, and as shown can extend at least 360° around the wearer's arm.

The secondary intermediate part 253 can extend laterally from the secondary posterior end 251, where the strap can originate, over a posterior portion 230P of the sleeve or base upper portion 231. It further transitions rearward to anterior portion 230A of the base or the upper portion 231 of the sleeve. The intermediate part 253 can extend laterally over the glenohumeral joint 105G, crossing the joint at a first elevation E1, as the part extends toward the anterior 230A of the base. Optionally, at this elevation E1, on the lateral and/or superior portion of the sleeve 230, for example, in the upper portion 233 of the sleeve, the intermediate part 253 of the posterior strap can traverse over and/or under the intermediate part 243 of the anterior strap 240. In this case, the respective channels routing the anterior strap and posterior strap can pass over one another, or can form a common channel for a small distance, depending on the application.

The intermediate part 253 of the posterior stability strap 250 can include a first intermediate part 253A that extends along a portion of the anterior 230A of the sleeve and/or the base before extending rearward again, optionally in a curved manner, toward the posterior of the sleeve and/or base and generally the midline M of the arm. This first intermediate part 253A can generally be disposed on the medial M1 side of the midline M of the sleeve or arm. The first end can be on a portion of the medial side M1, but optionally extends onto the lateral side L1 to the extent the midline M is relevant in the location where the posterior end is located.

Returning to the first intermediate part 253A, it transitions rearward over the biceps of the wearer 100, crossing the midline M of the arm and thus traversing a portion of the posterior 230P of the sleeve. The elevations and their distance of separation are described above. The posterior strap 250 in this location reroutes to extend posteriorly rearward, back across the glenohumeral joint 105G, and optionally slightly inferior to it. The posterior strap in that location also can be disposed at a second lower elevation E2, which is inferior to the first elevation E1. At the second lower elevation E1, the posterior strap 250 and in particular the intermediate part 253 of the posterior strap can traverse over and/or under the first intermediate part 243 of the anterior strap. Thus, in some cases the anterior and posterior straps can cross transversely to one another one, two or three times in the orthosis. Optionally, the anterior strap and posterior strap, and the respective first and second channels of the sleeve, can be symmetric about the coronal plane (or other plane parallel to it) that bisects the wearer into anterior and posterior portions. Further optionally, the routes of the straps and channels generally can be symmetric about that plane.

As shown in FIG. 17, the first intermediate part 253A can transition to a second intermediate part 253B which can be disposed on the medial M1 side of the midline M of the arm on the posterior 230P of the sleeve. The second intermediate part 253 can wind around and under the wearer's arm to the anterior of the sleeve. In so doing, it transitions to a third intermediate part 253C which extends back rearward, toward the midline M as well as the lateral portion of the wearer's forearm. The third intermediate part 253C can extend to the secondary inferior end 252 which as shown can extend to the lateral portion of the sleeve on the lateral side L1 of the midline M. There, the posterior stability strap 250 can engage a second anchor 254A that is associated with and/or joined with the anti-ride up element 232 of the sleeve, which is secured to the wearers forearm, generally inferior to the elbow 103. The second anchor 254A can be similar to the anchor 244A described above. Generally, the posterior stability strap can provide anterior/inferior support. It also can enable the secondary inferior end to be adjustably joined with the sleeve so that a preselected tension in the posterior stability strap can be adjusted. As mentioned above, the second channel of the sleeve can follow a virtually identical path as that described above in connection with the posterior stability strap and its different components.

Optionally, similar to the shoulder brace embodiment above, the intermediate part 253 between the strap ends can be configured to stretch and to store a tension force generally within the posterior stability strap, between those respective first and second ends 251, 252.

As shown in FIGS. 15-17, the orthosis 210 optionally can include an integral shoulder compression mitt 280. This mitt 280 can provide similar support as the humeral head stability strap 80 described in the shoulder brace embodiment above. In particular, this mitt can provide uniform tension and can pull the humeral head directly into the glenohumeral joint. The mitt 280 as shown can include a connector strap 281 that extends from the anterior 230A of the base or sleeve to the posterior 230P of the base or sleeve. For example, the connector strap 281 can include a first end 281E1 located on the anterior of the base or sleeve. This first end 281E1 can be anchored to the anterior of the base or sleeve. Optionally, it can include an adjustment mechanism to allow the attachment point to the base or sleeve to be adjusted in a superior and/or inferior direction to fit the anatomy of the wearer. This adjustment mechanism can be of the type described herein.

The connector strap 281 can include an intermediate part 281I that extends, across the shoulder laterally, to the posterior of the base or sleeve. The intermediate part 281I can be transverse to and can cross above and/or under the respective anterior stability strap 240 and the posterior stability strap 250. The respective channels of the sleeve that house these other straps can pass above and/or below the intermediate part 281I, depending on the application. In some cases, the sleeve 230 can include a separate channel for the connector strap 281. This channel likewise can pass above and/or below the respective channels for the anterior posterior stability straps, or can be common with these channels in select locations. The intermediate part 281I can extend to and terminate at the second end 281E2 located on the posterior 230P. This second end 281E2 can be anchored to the posterior 230P. Optionally, the second end can include an adjustment mechanism to allow the attachment point to the base or sleeve to be adjusted in a superior and/or inferior direction to fit the anatomy of the wearer. This adjustment mechanism, like the one at the first end, can be any of the fastener mechanisms or adjustment mechanisms mentioned herein.

In some applications, the mitt 280 can include a superior strap 280S and an inferior strap 280I that connect to the base and/or the sleeve. These straps can be used to pull the sleeve over the shoulder, under tension so that the sleeve itself, and optionally the connector strap, urges the humeral head into the glenohumeral joint. Optionally, the superior strap 280S can be in the form of a strap that is folded over upon itself, optionally with the portions of the anterior strap and posterior strap freely disposed between the fold parts of the superior strap 280S at one end. In some cases, the superior strap 280S also can extend to and can be joined with the connector strap 281. The superior strap 280S can include a proximal adjustment anchor 282. The adjustment anchor can be superior to the glenohumeral joint, the humeral head and, optionally, the elevation E1 shown in FIG. 15. The adjustment anchor can be a buckle, a hook and loop fastener system, a cam, or any of the other fastening or adjustment mechanisms mentioned herein. This can enable the wearer to adjust the overall length between connection points of the superior strap with the sleeve or base to thereby pull or release the sleeve and mitt over the humeral head and set it in an appropriate spatial orientation relative to the glenohumeral joint.

The inferior strap 280I can include a distal adjustment anchor 283. This distal adjustment anchor 283 can be inferior to the glenohumeral joint 105G and humeral head, and, optionally, superior to the elbow. The distal adjustment anchor 283 can be disposed below the elevation E1 and below the elevation E2 in some cases. It also can be attached to the lateral portion of the sleeve on the lateral side L1 of the midline M. The distal adjustment anchor 283 can be a buckle, a hook and loop fastener system, a cam, or any of the other fastening or adjustment mechanisms mentioned herein. This feature can enable the wearer to adjust the overall length between connection points of the inferior strap with the sleeve or base to thereby pull or release the sleeve and mitt over the humeral head and set it in an appropriate spatial orientation relative to the glenohumeral joint. In some cases, the proximal 282 and distal 283 adjustment anchors can be adjusted in unison to provide the suitable amount of compression and pull of the humeral head. It will further be appreciated that the sleeve and mitt can define respective channels for the inferior and superior straps. These channels can expose and/or can open externally to provide access to the respective anchors and straps, so that a user can adjust the respective length of those straps. Indeed, this fastener can be used in connection with any other strap or channel described herein.

The compression mitt 280, its connector strap 281, proximal anchor 282 and distal anchor 283 can be integral with the sleeve 230 such that the respective straps run through respective channels defined by the sleeve, with the sleeve and at least one of its layers operating in conjunction with the straps to exert forces on the humeral head relative to the glenohumeral joint. Due to the low profile of the mitt or portion of the sleeve that forms the mitt, and the containment of the straps in the mitt, these components are resistant to bunching when the wearer's arm is raised. In turn, this can prevent these components from impairing the wearer's ability to raise their arm laterally. The mitt also can provide resistance across the anterior and posterior of the shoulder, as well as across the top of the shoulder to produce an evenly distributed tension or force across the shoulder.

Optionally, the mitt and it strap can be configured to provide a "hard stop" to arrest external rotation of the humeral head and generally the shoulder. As an example, when the mitt is properly placed over the wearer shoulder, and the shoulder begins to externally rotate, the mitt can prevent that rotation beyond a certain angular orientation that may be detrimental to the structure and or condition of the glenohumeral joint 105 and/or the humeral head. For example, the mitt and strap can be configured to prevent external rotation beyond a certain angular orientation, such as beyond 20°, beyond 30°, beyond 40°, beyond 50° or other angles, depending on the condition of the user's shoulder and glenohumeral joint. To provide this hard stop to external rotation, the first end 281E1 and/or the intermediate part 281I can be constructed from elastic material that only stretches a certain amount, then ceases stretching. Thus, when those elements are stretched to a predetermined amount, they will stretch no more. This, in turn, will arrest the external rotation and provide the hard stop via the mitt. In other cases, the connector strap and its components can be constructed from generally elastic material. A second strap 281HS, constructed from an inelastic or less elastic material, can be stitched at its ends to the first end and the intermediate strap. This second strap can be of a length between the ends that are stitched or otherwise secured to the other straps. Upon a predetermined amount of external rotation, this strap will become taut, and due to its connection to the connector strap, and optionally the sleeve, at that point, it will arrest the external rotation because it is inelastic. Of course, as desired, this hard stop feature of the mitt can be modified or even deleted from the orthosis, depending on the application.

In a third alternative embodiment of the orthosis shown in FIGS. 20-23, the shoulder compression mitt can take on a different form. In that embodiment, the components of the orthosis 310 are virtually identical in structure, operation and function to the embodiment shown in FIGS. 15-18, and will not be described again here, with the exception of the mitt 380. The shoulder compression mitt 380 can be a modular mitt that can be installed or uninstalled relative to the sleeve 330 and its components. Thus, the modular mitt can be an add-on feature to the orthosis in certain applications. The sleeve can include a front connector strap 381 and a rear connector strap 384, which each can be connected to respective anterior and posterior parts of the base via anchors that are similar to those of the connector strap 381 in the embodiment above. The anchors can include adjustment mechanisms like those in the embodiments above that are releasable from the respective portions of the base and/or sleeve, so that the mitt can be removed from the same in certain applications.

Figure 22:
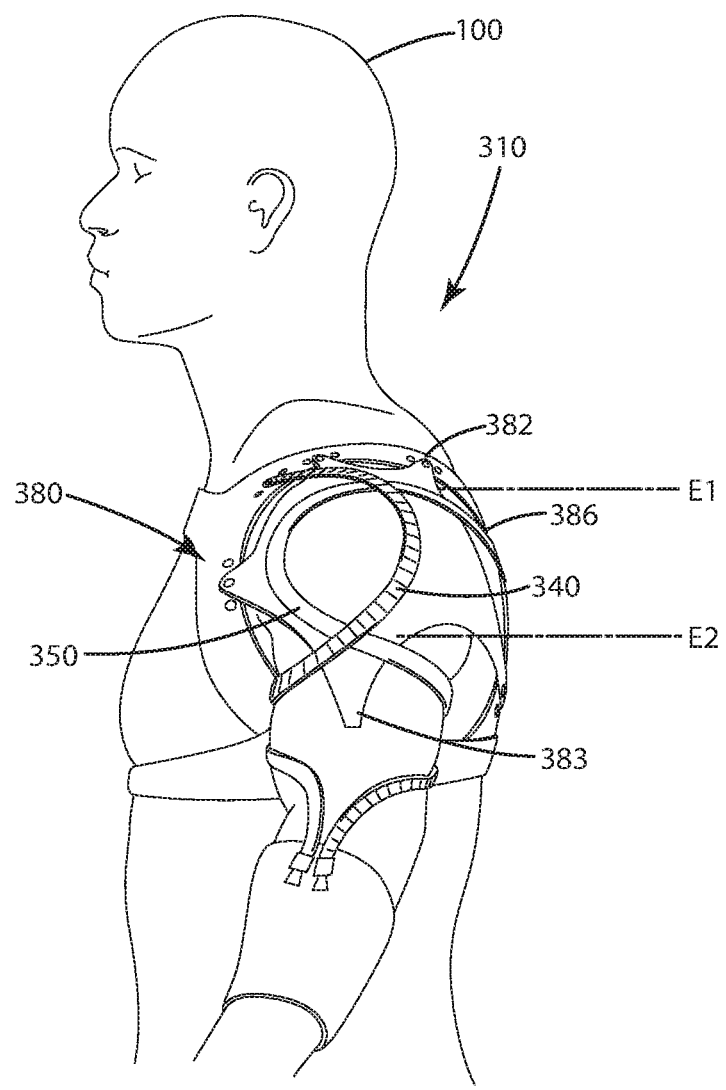
FIG. 22 is a side view thereof.
Figure 23:
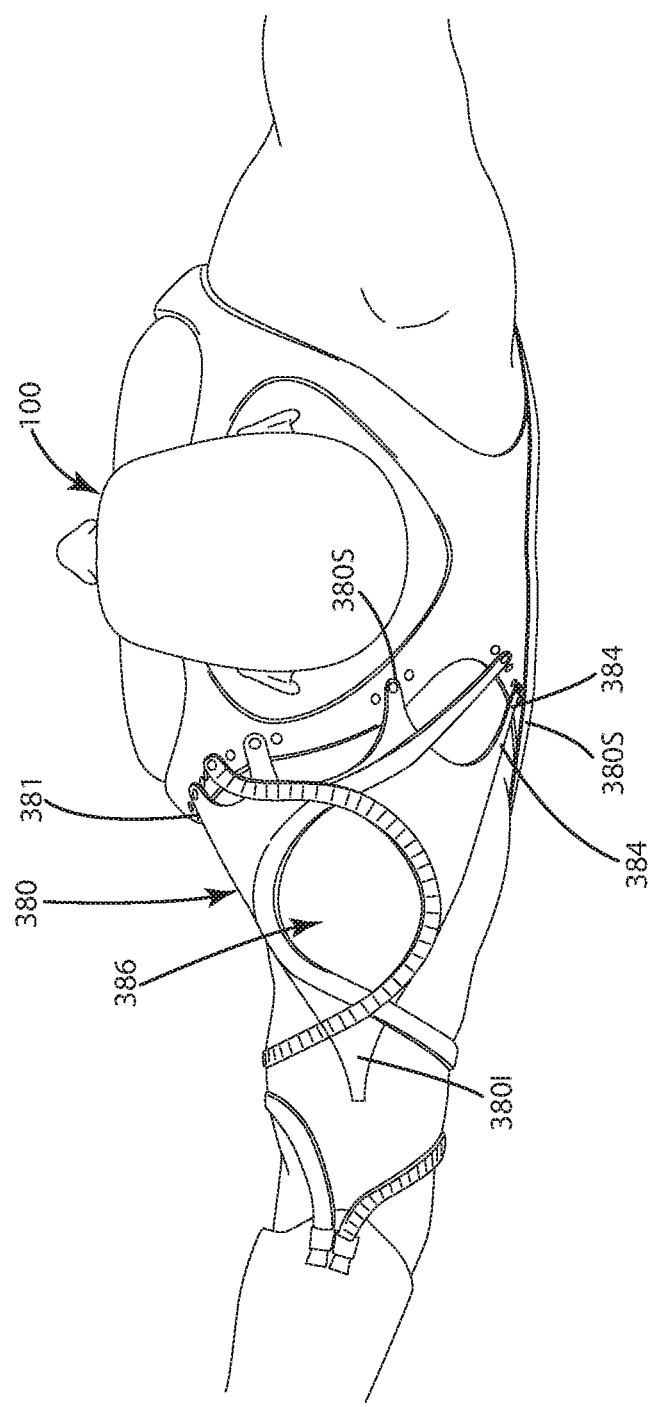
FIG. 23 is a top view thereof.

The front 381 and rear 384 connector straps however can be joined with a mitt main body 386 which can be in the form of a sheet or large strip that is integral with these straps. This sheet can be constructed from a knitted or woven fabric, or other elastomeric or flexible material, such as Neoprene®. All the components, that is, the body and straps, can be joined together as a monolithic or single piece unit that is removable and installable relative to the sleeve 330. The main mitt body 386 can extend over the anterior 340 and posterior 350 straps, and generally over the glenohumeral joint. As shown in FIG. 22, the main mitt body 386 can extend over both the anterior 340 and posterior 350 straps, optionally at both elevations E1 and E2, where those straps are transverse to one another. In some cases, the straps and the main mitt body 386 can operate in unison to provide stability to the joint.

In some applications, the mitt 380 can include superior 380S and inferior 380I straps that connect the main mitt body 386 to the base and/or the sleeve. These straps also can be integral with the main the mitt body, so that the components all form a single piece unit. These straps can be used to pull the mitt body under tension to urge the humeral head into the glenohumeral joint. Optionally, the superior strap 380S can include a proximal adjustment anchor 382. This adjustment anchor can be superior to the glenohumeral joint and the humeral head. This adjustment anchor also can be above the elevation E1 shown in FIG. 22. This adjustment anchor can be similar to any of the other anchors, fastening or adjustment mechanisms mentioned herein. This can enable the wearer to adjust the position of the main body 386 of the mitt. This adjustment anchor 382 also can be removable and/or detachable relative to the base and/or sleeve to facilitate removal of the modular mitt 380.

Optionally, the inferior strap 380I can include a distal adjustment anchor 383. This distal adjustment anchor 383 can be inferior to the glenohumeral joint 105G and humeral head, optionally superior to the elbow. This distal adjustment anchor can be disposed below the elevation E1 and below the elevation E2 in some cases. It also can be attached to the lateral portion of the sleeve on the lateral side L1 of the midline M. This distal adjustment anchor 383 can be a buckle, a hook and loop fastener system, a cam, or any of the other fastening or adjustment mechanisms mentioned herein. This can enable the wearer to adjust the position and orientation of the main mitt body 386 over the humeral head and the glenohumeral joint. The distal adjustment anchor 383 also can be removable and detachable relative to the sleeve, to facilitate removal of the mitt therefrom and its modular form. In some cases, the proximal 382 and distal 383 adjustment anchors can be adjusted in unison to provide the suitable amount of compression and pull of the humeral head.

Optionally, the mitt 380 can be constructed or can include a strap that provides a hard stop to arrest external rotation of the humeral head and generally the shoulder. For example, the front connector strap 381 can be inelastic after stretched a certain amount, or a can include another secondary strap thereover that is inelastic and connected at separate ends relative to the front connector strap 381 ends or the main mitt body 386.

Other alternative embodiments of the orthosis are contemplated. In one embodiment, any of the posterior, anterior and/or humeral head stability straps can be constructed from an inelastic material, rather than an elastic material. In this case, any one of the straps can be designated as an immobilizing strap to control and limit the range of motion of the joint, for example the glenohumeral joint. The current embodiments above can be outfitted so that the elastic straps are substituted with one or more inelastic straps, adjustable or not, to provide such immobilization.

In another embodiment, any adjustment anchors can include padding disposed over the same and/or around those anchors to prevent injury to the wearer upon heavy impact when the orthosis is worn in contact sports. In yet another embodiment, a thin sleeve or shirt is integrated into the orthosis to cover the respective straps and anchors. This covering can ensure that other players or individuals do not snag a digit in the straps or anchors and are not injured by the anchors.

In yet another embodiment, any one of the anterior, posterior and/or glenohumeral head straps can include indicia along the length. This indicia can be in the form of alphanumeric elements and/or in the form of color coding on the straps. This can provide feedback to the user and/or wear as to the degree of adjustment of the straps during such adjustment. Optionally, the orthosis can include a spring-loaded dial in line with the straps and integrated into the anchors to provide precise registration of the tension force stored in the respective straps.

In still another alternative embodiment, the lower arm portion can extend all the way down to a wrist of the wearer. Further optionally, the base can be in the form of a full shirt with both arms.

It still another embodiment, the orthosis can include a removable pad that is disposed on the shoulder region of the base for players with instability, to disperse impact forces. The pad can be fastened to the base and/or the bolster element using a variety of fasteners such as those described herein. In still another embodiment the base and sleeve can be perforated or otherwise include venting throughout the chest and back to increase breathability. Alternative breathable materials and/or open mesh materials can be used to construct the base and/or sleeve.

In a further alternative embodiment the base anterior and/or posterior portions can include a lacing system similar to a girdle or a back brace to enable a user to don the orthosis.

In yet another alternative embodiment, any anchors can be constructed to include a quick release so that the straps are easier to loosen and tighten, and thus take off or remove the orthosis. In some cases, the quick release can be in the form of a hook on the bottom of the anchor. In other cases, the quick release can be in the form of a buckle at the anchor.

The openings in the strap that engage the buckle can be numbered so that a wearer can consistently replace the strap at the correct tension. In a further embodiment, the respective stability straps can be of a variety of cross-sections, for example flat (as shown) or round. The resistant straps themselves may connect to an inelastic webbing to provide more consistent adjustment and prevent unnecessary stretching at locations where the straps engage anchors.

In still a further alternative embodiment, the orthosis can be in the form of a shirt. The shirt can be constructed from an engineered mesh material to control tension forces along lines discussed herein. In this construction, for example the textile over the shoulder and arm can mimic the support provided by the glenohumeral ligaments to provide desired support and to address instability and/or joint laxity.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. An orthosis comprising:
    a base that includes a torso portion configured to extend around a torso of a wearer and a shoulder portion configured to extend over a shoulder of the wearer, the base configured to secure the orthosis to the wearer;
    a sleeve extending from the base at the shoulder portion, the sleeve including a sleeve upper arm portion and a sleeve lower arm portion, the sleeve upper arm portion configured to extend over an upper arm of the wearer, the sleeve lower arm portion configured to extend over a lower arm of the wearer, beyond an elbow of the wearer, the sleeve lower arm portion including an anti-ride up element and terminating at an opening configured to receive a portion of the wearer's arm therethrough, the anti-ride up element being tapered along a length extending away from the upper arm portion so that a first dimension of the anti-ride up element adjacent the upper arm portion is greater than a second dimension of the anti-ride up element adjacent the opening, and so that the anti-ride up element prevents the sleeve from riding up an arm of the wearer from an inferior position to a superior position along the arm;
    an anterior stability strap having an primary anterior end and a primary inferior end, the primary anterior end being anchored to the shoulder portion of the base on an anterior of the base, adjacent the shoulder portion, the anterior stability strap including a primary intermediate part that extends from the primary anterior end, over an anterior of the sleeve upper portion, and transitions rearward to a posterior portion of the sleeve, extending over the posterior portion to the primary inferior end which is disposed adjacent the sleeve lower arm portion, the primary inferior end being adjustably joined with the sleeve so that a preselected tension in the anterior stability strap can be adjusted, thereby providing inferior and posterior support to a glenohumeral joint of the wearer;
    a posterior stability strap having a secondary posterior end and a secondary inferior end, the secondary posterior end being anchored to the shoulder portion of the base on a posterior of the base, adjacent the shoulder portion, the posterior stability strap including a secondary intermediate part that extends from the secondary posterior end, over a posterior of the sleeve upper portion and transitions forward to an anterior portion of the sleeve, extending over the anterior portion to the secondary inferior end which is disposed adjacent the lower portion of the sleeve, the secondary inferior end being adjustably joined with the sleeve so that a preselected tension in the posterior stability strap can be adjusted, thereby providing anterior and inferior support to the glenohumeral joint of the wearer,
    wherein at least one of the anterior stability strap and the posterior stability strap includes a working length between a first anchor and a distal, second anchor to which the at least one of the anterior stability strap and the posterior stability strap joins with the sleeve,
    wherein the working length is not altered when a tension force in at least one of the anterior stability strap and the posterior stability strap is changed from a first force to a greater second force.

2. The orthosis of claim 1 comprising:
    an anterior first anchor fixedly and immovably joined with the anterior portion of the sleeve, the anterior first anchor defining a first anterior anchor channel,
    wherein the primary intermediate part is slidably disposed in the first anterior anchor channel on the anterior portion of the sleeve.

3. The orthosis of claim 2,
    wherein the anterior first anchor is at least one of stitched, welded and adhered permanently to the anterior portion of the sleeve so that the first anchor cannot be removed from the sleeve without destroying at least one of the sleeve and the anterior first anchor.

4. The orthosis of claim 2 comprising:
a posterior first anchor fixedly and immovably joined with the posterior portion of the sleeve, the posterior first anchor defining a first posterior anchor channel,
wherein the secondary intermediate part is slidably disposed in the first posterior anchor channel on the posterior portion of the sleeve.

5. The orthosis of claim 1,
wherein the sleeve, the anterior stability strap and the posterior stability strap are configured to be disposed on a first side of a sagittal plane of the wearer, without extending to an opposing second side of the wearer.

6. The orthosis of claim 1 comprising:
a first humeral head stability strap having a first upper end and a first lower end, the first upper end being fixedly anchored to the shoulder portion of the base between the anterior and posterior of the base, superior to the shoulder, the first humeral head stability strap including a first intermediate part that extends inferiorly downward from the first upper end, over a lateral side of the sleeve upper portion, and transitions to an inferior portion of the sleeve, configured to be disposed adjacent an elbow of the wearer, the first lower end being selectively joined with the sleeve so that a preselected tension in the first humeral head stability strap can be established by the wearer or a healthcare provider, thereby providing inferior and multi-directional support to a glenohumeral joint of the wearer.

7. The orthosis of claim 6 comprising:
a second humeral head stability strap having a second upper end and a second lower end, the first upper end being fixedly anchored to the shoulder portion of the base on the posterior of the base, superior to the shoulder, the second lower end being joined with the first intermediate part of the first humeral head stability strap;
a third humeral head stability strap having a third upper end and a third lower end, the third upper end being fixedly anchored to the shoulder portion of the base on the anterior of the base, superior to the shoulder, the third lower end being joined with the first intermediate part of the first humeral head stability strap;
whereby the second and third humeral head stability straps are configured to evenly provide tension across the anterior and posterior of the base,
wherein the first, second and third humeral straps are configured to form a "W" shape across the shoulder of the wearer.

8. The orthosis of claim 6 comprising:
a lateral first anchor fixedly and immovably joined with a lateral portion of the sleeve, the lateral first anchor being in the form of a first channel,
wherein the first intermediate part is slidably disposed in the first channel on the lateral portion of the sleeve.

9. An orthosis comprising:
a base that includes a torso portion configured to extend around a torso of a wearer and a shoulder portion configured to extend over a shoulder of the wearer, the base configured to secure the orthosis to the wearer;
a sleeve extending from the base at the shoulder portion, the sleeve including a sleeve upper arm portion and a sleeve lower arm portion, the sleeve upper arm portion configured to extend over an upper arm of the wearer, the sleeve lower arm portion configured to extend over a lower arm of the wearer, beyond an elbow of the wearer, the sleeve lower arm portion including an anti-ride up element and terminating at an opening configured to receive a portion of the wearer's arm therethrough, the anti-ride up element being tapered along a length extending away from the upper arm portion so that a first dimension of the anti-ride up element adjacent the upper arm portion is greater than a second dimension of the anti-ride up element adjacent the opening, and so that the anti-ride up element prevents the sleeve from riding up an arm of the wearer from an inferior position to a superior position along the arm;
an anterior stability strap having an primary anterior end and a primary inferior end, the primary anterior end being anchored to the shoulder portion of the base on an anterior of the base, adjacent the shoulder portion, the anterior stability strap including a primary intermediate part that extends from the primary anterior end, over an anterior of the sleeve upper portion, and transitions rearward to a posterior portion of the sleeve, extending over the posterior portion to the primary inferior end which is disposed adjacent the sleeve lower arm portion, the primary inferior end being adjustably joined with the sleeve so that a preselected tension in the anterior stability strap can be adjusted, thereby providing inferior and posterior support to a glenohumeral joint of the wearer;
a posterior stability strap having a secondary posterior end and a secondary inferior end, the secondary posterior end being anchored to the shoulder portion of the base on a posterior of the base, adjacent the shoulder portion, the posterior stability strap including a secondary intermediate part that extends from the secondary posterior end, over a posterior of the sleeve upper portion and transitions forward to an anterior portion of the sleeve, extending over the anterior portion to the secondary inferior end which is disposed adjacent the lower portion of the sleeve, the secondary inferior end being adjustably joined with the sleeve so that a preselected tension in the posterior stability strap can be adjusted, thereby providing anterior and inferior support to the glenohumeral joint of the wearer; and
wherein the primary anterior end is configured to attach to the base adjacent an anterior deltoid of the wearer,
wherein the primary intermediate part is routed by a first anterior anchor channel downward inferiorly over a biceps head of the wearer, and is configured to extend downward inferiorly over a triceps head of the wearer,
wherein the primary inferior end is configured to join with the sleeve adjacent an elbow of the wearer.

10. An orthosis comprising:
a base that includes a torso portion configured to extend around a torso of a wearer and a shoulder portion configured to extend over a shoulder of the wearer, the base configured to secure the orthosis to the wearer;
a sleeve extending from the base at the shoulder portion, the sleeve including a sleeve upper arm portion and a sleeve lower arm portion, the sleeve upper arm portion configured to extend over an upper arm of the wearer, the sleeve lower arm portion configured to extend over a lower arm of the wearer, beyond an elbow of the wearer, the sleeve lower arm portion including an anti-ride up element and terminating at an opening configured to receive a portion of the wearer's arm therethrough, the anti-ride up element being tapered along a length extending away from the upper arm portion so that a first dimension of the anti-ride up element adjacent the upper arm portion is greater than a second dimension of the anti-ride up element adjacent the opening, and so that the anti-ride up element prevents the sleeve from riding up an arm of the wearer from an inferior position to a superior position along the arm;

an anterior stability strap having an primary anterior end and a primary inferior end, the primary anterior end being anchored to the shoulder portion of the base on an anterior of the base, adjacent the shoulder portion, the anterior stability strap including a primary intermediate part that extends from the primary anterior end, over an anterior of the sleeve upper portion, and transitions rearward to a posterior portion of the sleeve, extending over the posterior portion to the primary inferior end which is disposed adjacent the sleeve lower arm portion, the primary inferior end being adjustably joined with the sleeve so that a preselected tension in the anterior stability strap can be adjusted, thereby providing inferior and posterior support to a glenohumeral joint of the wearer;

a posterior stability strap having a secondary posterior end and a secondary inferior end, the secondary posterior end being anchored to the shoulder portion of the base on a posterior of the base, adjacent the shoulder portion, the posterior stability strap including a secondary intermediate part that extends from the secondary posterior end, over a posterior of the sleeve upper portion and transitions forward to an anterior portion of the sleeve, extending over the anterior portion to the secondary inferior end which is disposed adjacent the lower portion of the sleeve, the secondary inferior end being adjustably joined with the sleeve so that a preselected tension in the posterior stability strap can be adjusted, thereby providing anterior and inferior support to the glenohumeral joint of the wearer; and a shoulder compression mitt joined with a base anterior via an anterior mitt strap and with a base posterior via a posterior mitt strap, the shoulder compression mitt extending generally across a glenohumeral joint of the wearer from the base anterior to the base posterior, wherein the shoulder compression mitt, the anterior stability strap and the posterior stability strap are all fixed in a respective permanent orientation relative to the sleeve and relative to one another, but wherein the anterior stability strap and the posterior stability strap are free to slide along a respective first fixed route and a second fixed route.

11. An orthosis comprising:
a base configured to wrap around a torso of a wearer, the base including a base anterior and a base posterior;
a sleeve joined with the base, the sleeve including an upper arm portion configured to engage an upper arm of the wearer, and a lower arm portion configured to engage a lower arm of the wearer, below an elbow of the wearer, the lower arm portion including an anti-ride-up element configured to prevent the sleeve from riding up an arm of the wearer from an inferior position to a superior position along the arm;
an anterior stability strap extending from the base anterior, configured to extend inferiorly downward, traversing from a first side of a midline of the arm to a second, opposing side of the midline, the anterior stability strap extending adjacent a posterior portion of the sleeve, the anterior stability strap being joined to the lower arm portion, inferior to the elbow of the wearer, the anterior stability strap constrained to extend along a permanent first fixed route so that the anterior stability strap cannot be re-routed along a route different from the first fixed route over the shoulder and over the sleeve; and
a posterior stability strap extending from the base posterior, configured to extend inferiorly downward, traversing from the second side of the midline to the first side of the midline, the posterior stability strap extending adjacent an anterior portion of the sleeve, the posterior stability strap being joined to the lower arm portion, inferior to the elbow of the wearer, the posterior stability strap constrained to extend along a permanent second fixed route so that the posterior stability strap cannot be re-routed along a route different from the second fixed route over the shoulder and the sleeve,
wherein at least one of the anterior stability strap and the posterior stability strap includes a working length between a first anchor and a distal, second anchor to which the at least one of the anterior stability strap and the posterior stability strap joins with the sleeve,
wherein the working length is not altered when a tension force in at least one of the anterior stability strap and the posterior stability strap is changed from a first force to a greater second force.

12. The orthosis of claim 11,
wherein the anterior stability strap is configured to be adjustable in tension along a first length so that a preselected tension in the anterior stability strap can be established, thereby providing inferior and posterior support to a glenohumeral joint of the wearer,
wherein the posterior stability strap is configured to be adjustable in tension along a second length so that a preselected tension in the posterior stability strap can be established, thereby providing anterior and inferior support to the glenohumeral joint of the wearer,
wherein the anterior stability strap and the posterior stability strap each include portions configured to slide relative to the sleeve.

13. The orthosis of claim 12, comprising:
a first end anchor joined with a first end of the anterior stability strap to fixedly secure the first end to the base anterior,
a second end anchor joined with a second end of the anterior stability strap to fixedly and selectively secure a portion of the second end to the sleeve,
wherein the first end anchor and second end anchor are configured to remain stationary relative to the wearer and to one another when the preselected tension in the anterior stability strap is established,
wherein the second end anchor is configured to facilitate adjustment of tension in the anterior stability strap along the permanent first fixed route.

14. An orthosis comprising:
a base configured to wrap around a torso of a wearer, the base including a base anterior and a base posterior;
a sleeve joined with the base, the sleeve including an upper arm portion configured to engage an upper arm of the wearer, and a lower arm portion configured to engage a lower arm of the wearer, below an elbow of the wearer, the lower arm portion including an anti-ride-up element configured to prevent the sleeve from riding up an arm of the wearer from an inferior position to a superior position along the arm;
an anterior stability strap extending from the base anterior, configured to extend inferiorly downward, traversing from a first side of a midline of the arm to a second, opposing side of the midline, the anterior stability strap extending adjacent a posterior portion of the sleeve, the anterior stability strap being joined to the lower arm portion, inferior to the elbow of the wearer, the anterior stability strap constrained to extend along a permanent first fixed route so that the anterior stability strap cannot be re-routed along a route different from the first fixed route over the shoulder and over the sleeve; and a posterior stability strap extending from the base posterior, configured to extend inferiorly downward, traversing from the second side of the midline to the first side of the midline, the posterior stability strap extending adjacent an anterior portion of the sleeve, the posterior stability strap being joined to the lower arm portion, inferior to the elbow of the wearer, the posterior stability strap constrained to extend along a permanent second fixed route so that the posterior stability strap cannot be re-routed along a route different from the second fixed route over the shoulder and the sleeve, wherein the anterior stability strap is elastic and configured to store a tension force, wherein the anterior stability strap is secured to the base at a first anchor and to the sleeve at a second anchor, wherein the distance between the first anchor and the second anchor remains substantially static, even when the tension force is changed from a first force to a greater second force.

15. An orthosis comprising:

a base configured to wrap around a torso of a wearer, the base including a base anterior and a base posterior;

a sleeve joined with the base, the sleeve including an upper arm portion configured to engage an upper arm of the wearer, and a lower arm portion configured to engage a lower arm of the wearer, below an elbow of the wearer, the lower arm portion including an anti-ride-up element configured to prevent the sleeve from riding up an arm of the wearer from an inferior position to a superior position along the arm;

an anterior stability strap extending from the base anterior, configured to extend inferiorly downward, traversing from a first side of a midline of the arm to a second, opposing side of the midline, the anterior stability strap extending adjacent a posterior portion of the sleeve, the anterior stability strap being joined to the lower arm portion, inferior to the elbow of the wearer, the anterior stability strap constrained to extend along a permanent first fixed route so that the anterior stability strap cannot be re-routed along a route different from the first fixed route over the shoulder and over the sleeve; and a posterior stability strap extending from the base posterior, configured to extend inferiorly downward, traversing from the second side of the midline to the first side of the midline, the posterior stability strap extending adjacent an anterior portion of the sleeve, the posterior stability strap being joined to the lower arm portion, inferior to the elbow of the wearer, the posterior stability strap constrained to extend along a permanent second fixed route so that the posterior stability strap cannot be re-routed along a route different from the second fixed route over the shoulder and the sleeve; and a shoulder compression mitt joined with the base anterior via an anterior mitt strap and with the base posterior via a posterior mitt strap, the shoulder compression mitt extending generally across a glenohumeral joint of the wearer, wherein the shoulder compression mitt, the anterior stability strap and the posterior stability strap are all fixed in a respective permanent orientation relative to the sleeve and relative to one another, but wherein the anterior stability strap and the posterior stability strap are free to slide along the respective first fixed route and the second fixed route.

16. The orthosis of claim 15, wherein the anterior stability strap is constrained to slide within a first channel defined by the sleeve along the permanent first fixed route, wherein the posterior stability strap is constrained to slide within a second channel defined by the sleeve along the permanent second fixed route, wherein the first and second channels extend away from and toward the midline of the arm along different portions of the first and second channels.

17. An orthosis comprising:

a base including a sleeve, the sleeve having a sleeve upper portion, a sleeve central portion and a sleeve lower portion, the sleeve including a base anterior and a base posterior, the sleeve upper portion configured to extend over an appendage of a wearer superior to a joint of the wearer, the sleeve central portion configured to extend over at least a portion of the joint, the sleeve lower portion configured to extend over the appendage inferior to the joint of the wearer, the sleeve lower portion forming an anti-ride up element and terminating at an opening configured to receive a portion of the wearer's appendage inferior to the joint therethrough, the anti-ride up element being tapered along a length extending away from the upper portion so that a first dimension of the anti-ride up element adjacent the upper portion is greater than a second dimension of the anti-ride up element adjacent the opening, and so that the anti-ride up element prevents the sleeve from riding up the appendage of the wearer from an inferior position to a superior position along the appendage;

a first stability strap selectively joined with the sleeve so that a preselected tension in the first stability strap can be established by adjusting a first tension in the first stability strap, thereby providing a first support to the joint of the wearer;

a first channel defined by the sleeve, the first stability strap being slidably disposed in the first channel so that the first stability strap can slide longitudinally within the sleeve along a first predetermined route;

a second stability strap selectively joined with the sleeve so that a preselected tension in the second stability strap can be established by adjusting a second tension in the second stability strap, thereby providing a second support to the joint of the wearer; and a second channel defined by the sleeve, the second stability strap being slidably disposed in the second channel so that the second stability strap can slide longitudinally within the sleeve along a second predetermined route; and a shoulder compression mitt including a connector strap that extends from a location on a base anterior, across the glenohumeral joint, to a base posterior, wherein the first stability strap and the second stability strap are configured to traverse over one another at a first elevation, wherein the first stability strap and the second stability strap are configured to traverse over one another again at a second elevation inferior to the first elevation.

18. The orthosis of claim 17,
wherein the first stability strap includes a first upper end and the second stability strap includes a second upper end, anchored to the base anterior at a shoulder portion of the base,
wherein the sleeve central portion is configured to extend over at least a portion of a glenohumeral joint.

\* \* \* \* \*